US012632596B2

(12) United States Patent
Li et al.

(10) Patent No.: US 12,632,596 B2
(45) Date of Patent: May 19, 2026

(54) SYSTEMS AND METHODS FOR SURGICAL VIDEO DE-IDENTIFICATION

(71) Applicant: SURGICAL SAFETY TECHNOLOGIES INC., New York, NY (US)

(72) Inventors: Tianbao Li, Toronto (CA); Shuja Khalid, Toronto (CA); Kevin Yang, Toronto (CA); Frank Rudzicz, Toronto (CA); Teodor Pantchev Grantcharov, Stouffville (CA)

(73) Assignee: SURGICAL SAFETY TECHNOLOGIES INC.

( * ) Notice: Subject to any disclaimer, the term of this patent is extended or adjusted under 35 U.S.C. 154(b) by 145 days.

(21) Appl. No.: 18/037,990

(22) PCT Filed: Nov. 22, 2021

(86) PCT No.: PCT/CA2021/051658
§ 371 (c)(1),
(2) Date: May 19, 2023

(87) PCT Pub. No.: WO2022/104484
PCT Pub. Date: May 27, 2022

(65) Prior Publication Data
US 2023/0409749 A1     Dec. 21, 2023

Related U.S. Application Data

(60) Provisional application No. 63/116,582, filed on Nov. 20, 2020.

(51) Int. Cl.
*G06F 21/62*          (2013.01)
*A61B 90/00*         (2016.01)
(Continued)

(52) U.S. Cl.
CPC ........ *G06F 21/6254* (2013.01); *A61B 90/361* (2016.02); *G06T 7/20* (2013.01);
(Continued)

(58) Field of Classification Search
CPC ... G06F 21/6254; A61B 90/361; G06V 20/70; G06V 2201/07; G06T 7/20; H04N 21/4318
(Continued)

(56) References Cited

U.S. PATENT DOCUMENTS 9,799,096 B1    10/2017  Torre et al.
10,242,282 B2 *  3/2019  Loce ................... G06F 21/6254
(Continued)

OTHER PUBLICATIONS

Canadian Intellectual Property Office (CIPO), International Search Report and Written Opinion to PCT/CA2021/051658, Feb. 1, 2022.
(Continued)

*Primary Examiner* — Michael R Vaughan
*Assistant Examiner* — Saad Ahmad Abdullah
(74) *Attorney, Agent, or Firm* — NZ Carr Law Office

(57)          ABSTRACT

An improved approach is described herein wherein an automated de-identification system is provided to process the raw captured data. The automated de-identification system utilizes specific machine learning data architectures and transforms the raw captured data into processed captured data by modifying, replacing, or obscuring various identifiable features. The processed captured data can include transformed video or audio data.

20 Claims, 29 Drawing Sheets

(51) Int. Cl.
  *G06T 7/20* (2017.01)
  *G06V 20/70* (2022.01)
  *H04N 21/431* (2011.01)

(52) U.S. Cl.
  CPC ......... *G06V 20/70* (2022.01); *H04N 21/4318*
      (2013.01); *G06V 2201/07* (2022.01)

(58) Field of Classification Search
  USPC .......................................................... 726/26
  See application file for complete search history.

(56) References Cited

U.S. PATENT DOCUMENTS

| | | | | |
|---|---|---|---|---|
| 11,170,309 B1* | 11/2021 | Stefani | ................ | H04L 63/0428 |
| 2010/0328436 A1* | 12/2010 | Skubic | ................. | A61B 5/0022 |
| | | | | 348/47 |
| 2020/0372180 A1* | 11/2020 | Venkataraman | .... | H04L 63/0407 |
| 2021/0327037 A1* | 10/2021 | Hares | ...................... | G06T 7/579 |
| 2022/0358773 A1* | 11/2022 | Thienphrapa | .... | A61B 1/000096 |

OTHER PUBLICATIONS

Bingquan Zhu, Hao Fang, Yanan Sui, and Luming Li, "Deepfakes for Medical Video De-Identification: Privacy Protection and Diagnostic Information Preservation", Proceedings of the AAAI/ACM Conference on AI, Ethics, and Society, Association for Computing Machinery, New York, NY, USA, pp. 414-420, Feb. 2020 (Feb. 2020), DOI: https://doi.org/10.1145/3375627.3375849.

* cited by examiner

200B

*Recall:* 20% *"1 out of 5 humans found"*

*Precision:* 98% Certainty of the pixels that correspond to a human

210

*Recall:* 100% *"All humans found"*

*Precision:* 12% *"uncertainty of what pixels correspond to a human"*

208

200D

*Recall:  100% "All humans found"*

*Precision:  96%  "uncertainty of what pixels correspond to a human"*

212

Interpolate by Momentum

1. IOU Tracker find bbox under id#x
2. Interpolate by average displacement
3. Predict bidirectional frames by average displacement $$\Delta x = \lambda \, (x_i - x_{i-1}) + (1-\lambda)\Delta x$$

10

5

-2

-1

1 #2 #3 #4 #5 #6 #7

$\Delta$old copy bbox on #0 to #(1,2,3,4)

600

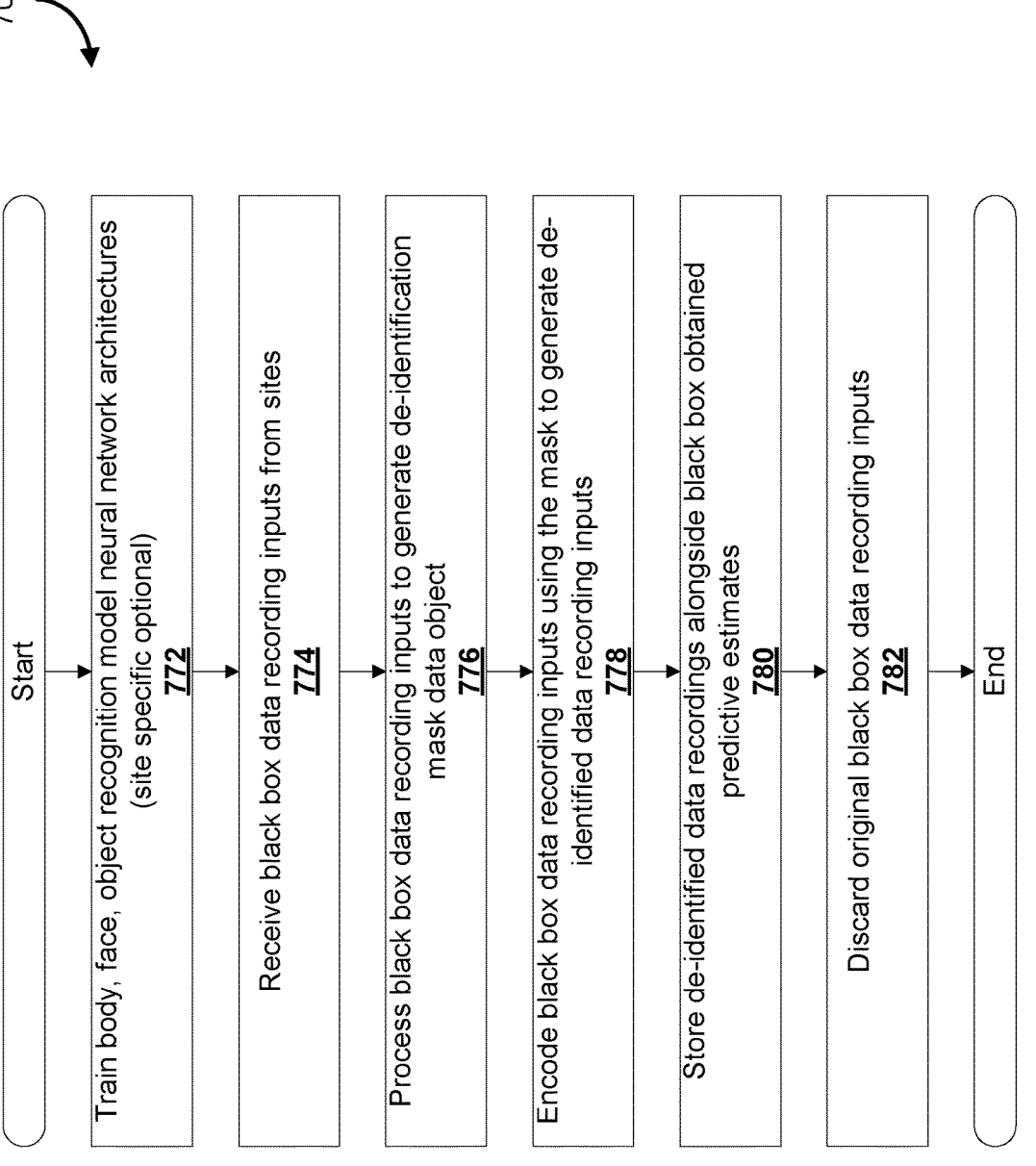

700B

Start

Train body, face, object recognition model neural network architectures (site specific optional) 772

Receive black box data recording inputs from sites 774

Process black box data recording inputs to generate de-identification mask data object 776

Encode black box data recording inputs using the mask to generate de-identified data recording inputs 778

Store de-identified data recordings alongside black box obtained predictive estimates 780

Discard original black box data recording inputs 782

End

Figure 13:
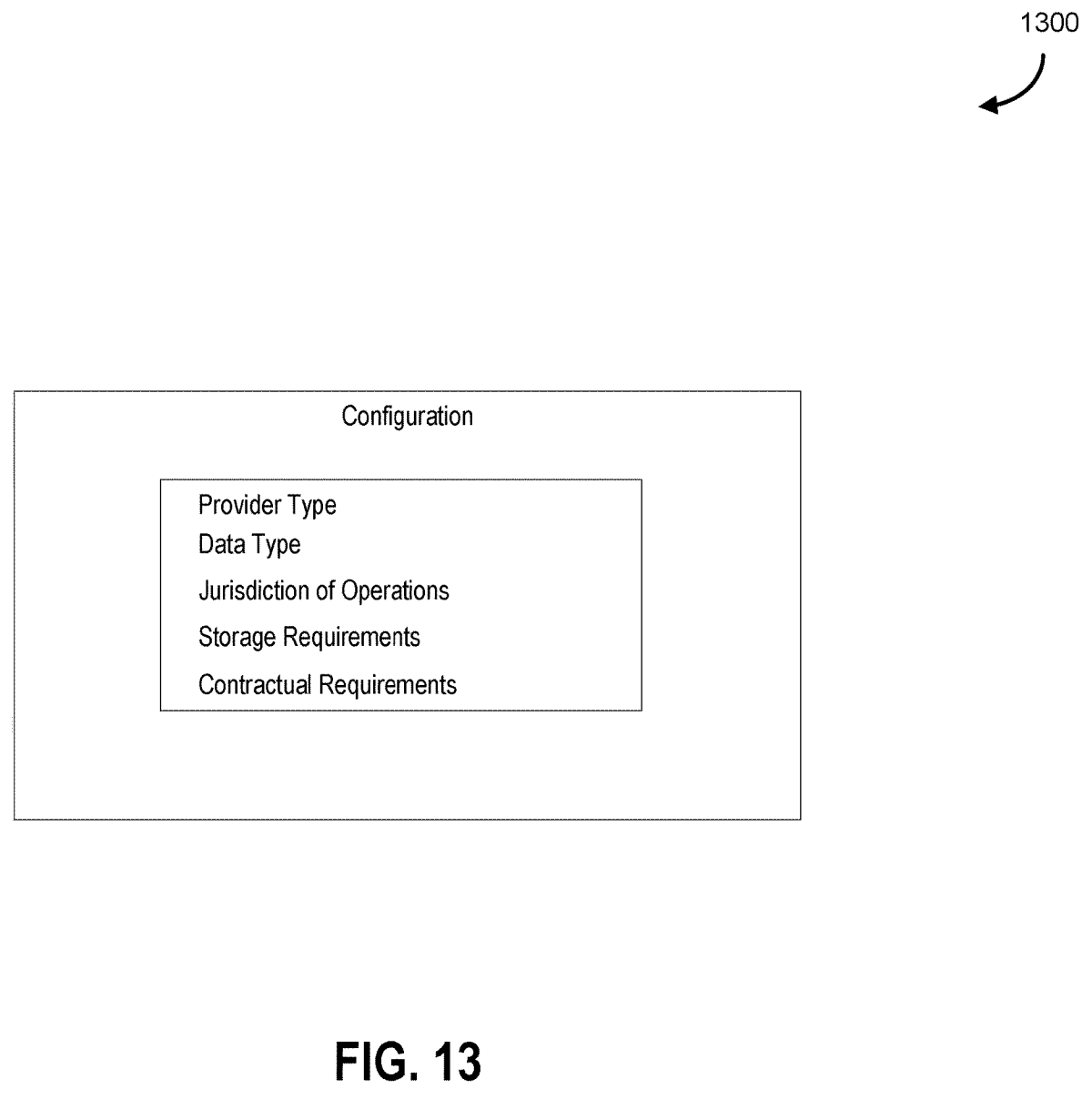

Configuration

Provider Type
Data Type
Jurisdiction of Operations
Storage Requirements
Contractual Requirements

| 0 | 0.3 | 0.3 | 0 | 0 | 0 | 0 | 0 | 0 | 0 | 0 | 1 | 1 | 0 | 0 |
|---|---|---|---|---|---|---|---|---|---|---|---|---|---|---|
| 0 | 0.3 | 0.3 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0.14 | 0.113 | 0.1 | 0 |
| 0 | 0 | 0 | 0 | 1 | 1 | 1 | 0.3 | 0.7 | 0 | 0 | 0.45 | 0.4 | 0.2 | 0 |
| 0 | 0 | 0 | 0 | 1 | 1 | 1 | 0.6 | 0.7 | 0.5 | 0.3 | 0.3 | 0.3 | 0.2 | 0 |
| 0 | 0 | 0 | 0 | 0 | 0 | 0 | 0 | 0 | 0 | 0 | 0.12 | 0.1 | 0.05 | 0 |

SYSTEMS AND METHODS FOR SURGICAL VIDEO DE-IDENTIFICATION

CROSS-REFERENCE

This application is a non-provisional of, and claims all benefit, including priority to, U.S. Application No. 63/116,582, filed 20 Nov. 2020, entitled "SYSTEMS AND METHODS FOR SURGICAL VIDEO DE-IDENTIFICATION", incorporated herein by reference in its entirety.

FIELD

Embodiments of the present disclosure relates to the field of machine learning, and more specifically, embodiments relate to devices, systems and methods for machine learning adapted to de-identify video data.

INTRODUCTION

Captured operating room (OR) video and data can include vast amounts of sensitive data. The data is sensitive as the data contains identifying characteristics such as faces, skin colour, gender based-attributes, distinctive symbols, ornaments, room markers, and vocal accents that may be used to identify individuals in the videos.

These identifying characteristics provide context that might not be necessary for clinical analysis and can thus be removed or obscured.

SUMMARY

The volume of data generated from videos, such as surgical videos, can be large. The data is useful for downstream analysis or playback, such as to conduct incident analyses, recognize practices that should be adopted or those that should be avoided, etc. For example, the data can be combined with post-operative data to identify practices that yielded faster recovery times, reduced adverse events, among others. This is particularly important in surgical situations where the skill and approach taken practitioners has a significant effect on the outcomes. Small variations in individual and team performances, as well as environmental and organization factors can contribute to potential patient harm.

In some embodiments, a synchronized recording system is provided that captures data from a treatment facility or location, such as an operating room. The approach is adapted for identifying, localizing, and tracking objects (e.g., individuals, equipment, or other objects). The data can be in the form of video and audio data, and in some embodiments, can include one or more high field of view cameras that are able to capture events taking place in the treatment facility or location.

A technical problem associated with the captured data is that it often includes identifiable information, such as visual/auditory characteristics of practitioners, patients, and other visual or audible artifacts (posters, decorations, clocks) from the treatment facility or location, and it may be desirable to process the raw captured data to remove such identifiable information (e.g., for privacy reasons or regulatory reasons). Computational processing to automatically remove (or flag) the identifiable information is especially desirable, such that a transformed video or audio can be automatically output having the machine identified features obscured, modified, or removed. In a variant embodiment, the transformed video or audio can be an intermediate output that can then be provided to a human quality reviewer who takes a final review of the pre-processed video before final output.

An objective is to generate a de-identified output data stream which cannot be easily reverse engineered to re-identify practitioners, patients, or, in some situations, a specific facility or specific procedure, while preserving relevant features that are useful for downstream analysis of the procedure itself (e.g., understanding what steps that a specific surgical team took that led to consistent superior post-operative outcomes).

Accordingly, extraneous identifiable data should be removed during processing. However, technical challenges further arise as there are limited computational resources available (especially if the processing is conducted on a real or near-real time basis), and there is a technical trade-off as removing identifiable information could lead to relevant information being removed, impacting the accuracy or usefulness of downstream analysis. Manual approaches are not practically feasible given a lack of review resources and may not be desirable given privacy concerns associated with human reviewers.

An improved approach is described herein wherein a computer-based automated de-identification system is provided to process the raw captured data. The automated de-identification system utilizes specific machine learning data architectures and transforms the raw captured data into processed captured data by modifying, replacing, or obscuring various identifiable features. The processed captured data can include transformed video or audio data.

In an embodiment, the automated de-identification system is adapted to track, in video data, objects within the field of view and visually replace them with alternate simplified graphical representations, such as pixel-based meshes, texture maps, contours, wireframes/skeletons, shaped blocks (e.g., for practitioner heads), replacement objects (e.g., cartoon bodies and block heads), blurred regions (e.g., patient genitals). These alternate graphical representations can be tracked as the visual objects move within the field of view or beyond the field of view, or as they become obstructed.

Approaches are described herein that relate to object tracking through, for example, momentum interpolation/extrapolation such that the alternate graphical representations are adapted to be maintained despite partial obstruction, etc., with an automatic bias towards prudence in de-identification (e.g., allowing a greater emphasis on true positives, biasing the system in favor of acceptable amounts of false negatives over reducing false positives) so that the risk of potential re-identification is minimized to the extent possible. There is a balance between precision and recall—and in some variations, these factors can be adjusted during the processing step.

Extrapolation techniques can include medium filtering, or improved variations that adapt to situations where the automated system fails to detect a particular object in a particular frame, but is configured to observe the context window around that frame, to interpolate that a particular section of a frame should be nonetheless transformed (e.g., blurred). Accordingly, for example, when there is movement, the contour and the head potentially can be seen to extend outside of the contour of the person, leaving a bulbous looking effect.

In a variant embodiment, approaches for audio de-identification are used separately or together with video de-identification. Audio de-identification can include obfuscation to remove identifiable auditory characteristics (e.g., distinct accents, stammers, tone, cadence, pitch, accentuation), for example, by replacing the audio with computer-generated voices or sampled voices, etc. Machine characteristics may also be replaced, for example, if there are vendor or device specific types of beeps or alert notification sounds. For the audio de-identification, in some embodiments, approaches are further described to maintain certain relevant characteristics that are useful for downstream analysis, such as periods of increased volume (e.g., yelling indicative of a situation or urgency), accentuation on various phrases, syllables, phonemes, or words (e.g., noting particular importance on those semantic objects). For example, computational models are described that allow one to speak into a neural network and the voice is modified to something else. If someone is speaking, the computational model can preserve tone of speech, sentiment, non technical skills while obscuring other identifiable aspects.

In another variant embodiment, approaches are described for a machine learning-based approach to interpret combinations of identifiable factors in the raw input data that can be used for potential identification of a particular procedure (e.g., heart valve replacement scheduled from 1:30 PM-2:00 PM in operating room 3) or a facility in which the procedure took place (e.g., heart valve replacement took place in hospital X). These identifiable factors can include visual or auditory aspects such as background information, such as labelling or signage in the background indicative of which operating room (e.g., OR-3) the procedure is taking place, identifiable décor (e.g., a pamphlet on hand-cleaning procedures at hospital X), identifiable clock designs, etc. Auditory aspects can include specific types of notification sounds, background equipment hums, periodic sounds, etc. Scene-based identifiable factors, in some embodiments, can be similarly obscured, replaced, removed, or modified. In a further embodiment, the system is adapted to track identifiable combinations and modify aspects of the combinations thereof such that it is more difficult to reverse engineer the de-identification.

In another variant embodiment, the system is adapted for operation in real or near-real time, while in other variant embodiments, the system is adapted for operation with a particular processing time (e.g., run overnight) or target processing objective (e.g., de-identification accuracy level at least greater than 98.5%). The operational characteristics, in some embodiments, can be tweaked based on desired output, for example, by modifying hyperparameters, such as sampling frequency, window size, a couple of graphs, among others.

In a further variant embodiment, an initial de-identification is conducted for real or near-real time audio or video output generation, generating a first-pass audio or video output. In this embodiment, the initial de-identification is adapted for a faster generation using limited computational time and resources, and can be biased towards allowing a greater amount of false negatives to be incorporated (e.g., more pixels or visual/audio artifacts being included for de-identification). In subsequent passes that are conducted, the de-identification may be conducted repeatedly on the output to reduce the amount of false negatives, and each subsequent pass may have less negatives than prior versions.

In another variant embodiment, the conversion is one-way, and the original audio or video is deleted or encrypted after an initial de-identification pass, after a number of de-identification passes have occurred, or after a period of time has elapsed.

Corresponding methods, and computer program products affixed in the form of non-transitory computer readable media having machine interpretable instruction sets stored thereon, which when executed by a processor, cause the processor to perform one or more methods associated with the de-identification of recorded data sets as described in various embodiments herein.

DESCRIPTION OF THE FIGURES

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures:

FIG. 7B is an example method diagram showing a method for de-identification, according to some embodiments.

FIGS. 13-16 show an example configuration model for an experimental setup, according to some embodiments.

DETAILED DESCRIPTION

Figure 1:
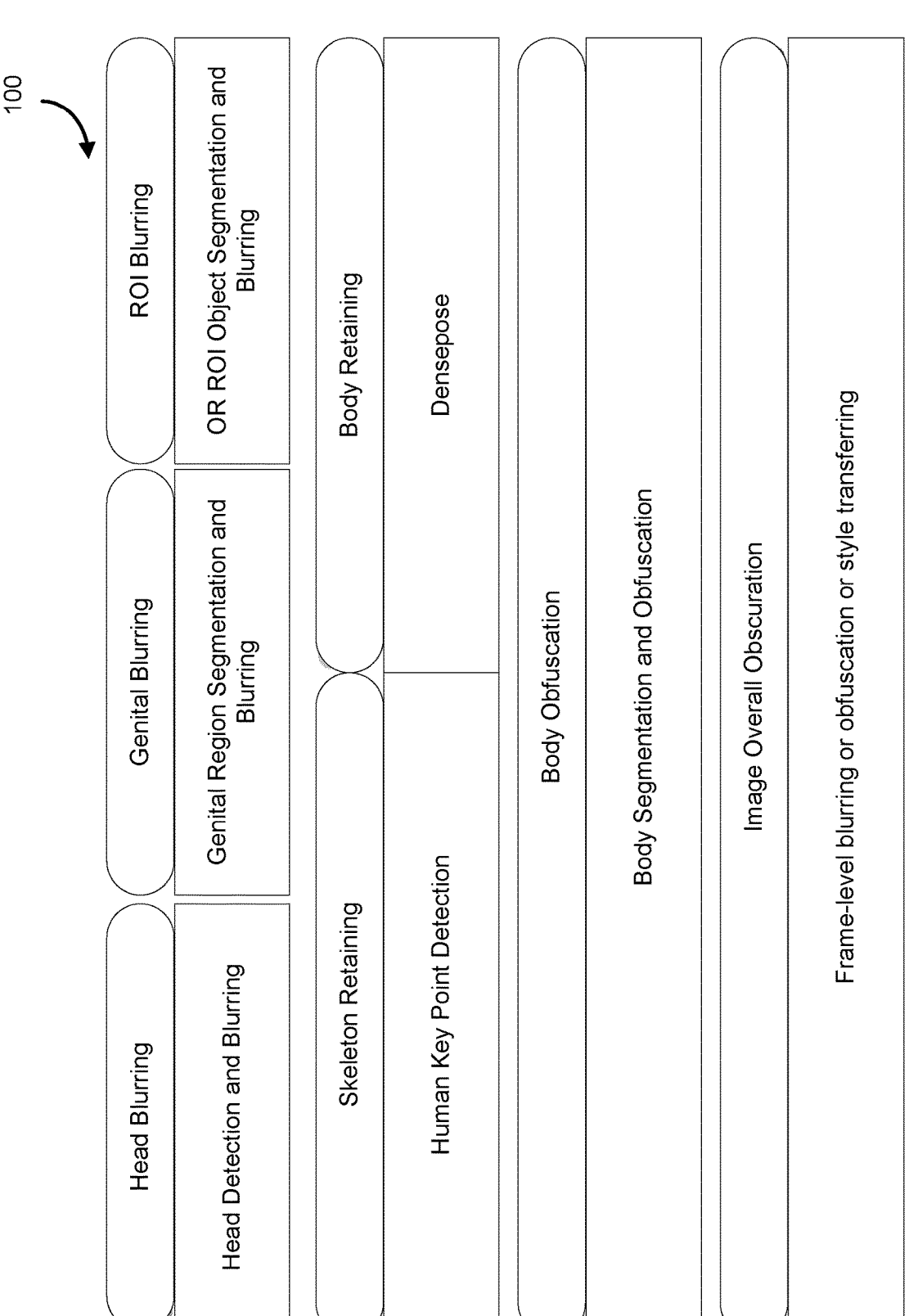
FIG. 1 is a chart showing aspects for de-identification as well as aspects for retaining for maintaining viability of a post-de-identification audio/video object for future analysis, according to some embodiments.

Systems, methods, and computer readable media storing machine-interpretable instruction sets are described in various embodiments herein that provide a computer-implemented automated de-identification mechanism that receives as inputs audio or video data objects, and generates transformed output audio or video data objects that have been modified to de-identify (in some embodiments, practically irreversibly through the loss or replacement of data) various aspects of the output audio or video data objects.

In an operating room recording platform, the operating room is captured by several cameras synchronously that give an overall view of various events occurring in the operating room. Reactions, movements, and co-ordinations are useful for surgical analysis but not identifiable features of humans which can cause privacy issues. De-identification on room video is transformed to blur or obscure image pixels that can help identify, but keep the information for surgical analysis as much as possible. Laparoscopic video is important for surgical analysis, especially for surgical technical skills. However, the surgical instruments with the camera are not inside the patient's body all the time. Accordingly, the surgical team can also be shown in the laparoscopic camera video when it is active and out of the body. To de-identify the laparoscopic videos, the system needs to identify whether each frame shows an internal view and external view and blur or totally remove the latter.

De-identification is particularly important in respect of sensitive information, such as recordings of surgical videos. This challenge is exacerbated when the volume of data generated from videos, such as surgical videos, can be large. The data is useful for downstream analysis or playback, such as to conduct incident analyses, recognize practices that should be adopted or those that should be avoided, etc. For example, the data can be combined with post-operative data to identify practices that yielded faster recovery times, reduced adverse events, among others. This is particularly important in surgical situations where the skill and approach taken practitioners has a significant effect on the outcomes. Small variations in individual and team performances, as well as environmental and organization factors can contribute to potential patient harm.

It is important to note that computational approaches are described that take a best effort approach to obscure the identifiable features in room videos, and the processing can be imperfect. Accordingly, the computational approach, after the automatic removal, can still have some identifiable features that are not properly removed, and this can occur, especially in relation to corner cases and insufficient training data. For the transformed (e.g., De-IDed) videos to be returned to clients, ideally they should be as close to 100% perfect as possible, without any heads or bodies visible without obfuscation, for example. Accordingly, the output from the system can be provided in the form of a first-pass transformed output (that can include corresponding metadata indicating areas of lower confidence) to aid in human analysts on quality assurance or downstream data processing engines. Downstream re-processing (e.g., "fine tuning") can then be used to collect feedback data where the model fails, and this can be used as to help in future training (e.g., improving the machine learning by using the past failures as training data for supervised training).

In some embodiments, a synchronized recording system is provided that captures data from a treatment facility or location, such as an operating room. The approach is adapted for identifying, localizing, and tracking objects (e.g., individuals, equipment, or other objects). The data can be in the form of video and audio data, and in some embodiments, can include one or more high field of view cameras that are able to capture events taking place in the treatment facility or location.

A technical problem associated with the captured data is that it often includes identifiable information, such as visual/auditory characteristics of practitioners, patients, and other visual or audible artifacts (posters, decorations, clocks) from the treatment facility or location, and it may be desirable to process the raw captured data to remove such identifiable information (e.g., for privacy reasons or regulatory reasons).

FIG. 1 is a chart showing aspects for de-identification as well as aspects for retaining for maintaining viability of a post-de-identification audio/video object for future analysis, according to some embodiments. In chart 100, the most important characteristics for de-identification and present approaches for their removal from video or audio clips is shown, according to some embodiments.

An objective is to generate a de-identified output data stream which cannot be easily reverse engineered to re-identify practitioners, patients, or, in some situations, a specific facility or specific procedure, while preserving relevant features that are useful for downstream analysis of the procedure itself (e.g., understanding what steps that a specific surgical team took that led to consistent superior post-operative outcomes).

Accordingly, it is desirable that extraneous identifiable data be removed during processing. However, technical challenges further arise as there are limited computational resources available (especially if the processing is conducted on a real or near-real time basis), and there is a technical trade-off as removing identifiable information could lead to relevant information being removed, impacting the accuracy or usefulness of downstream analysis. Manual approaches are not practically feasible given a lack of review resources and may not be desirable given privacy concerns associated with human reviewers.

For example, in chart 100, heads, genitals can be detected and obfuscated (e.g., blurred) from videos, or focus can be established over a region of interest with other background aspects obfuscated. Conversely, it may be useful to retain certain aspects of data that are useful for surgical performance analysis and/or comparisons with patient outcomes, and in some embodiments, the system is configured for retaining skeleton and/or body key point information while removing other, less useful features associated with bodies. Where a frame is not particularly relevant to an outcome, the entire frame could be obfuscated (e.g., empty operating room prior to procedure).

Chart 100 shows a hierarchy of values that can be utilized to prioritize and/or rank the importance of various outcomes for the transformed audio and/or video data. For each of the aspects to be de-identified, the features may be identified as one or more audio or visual artifacts present in various frames of the input video stream. The features can be tracked across a multitude of frames and obfuscated despite movements and changes in position, or leaving and entering a frame of view.

Figure 2A:
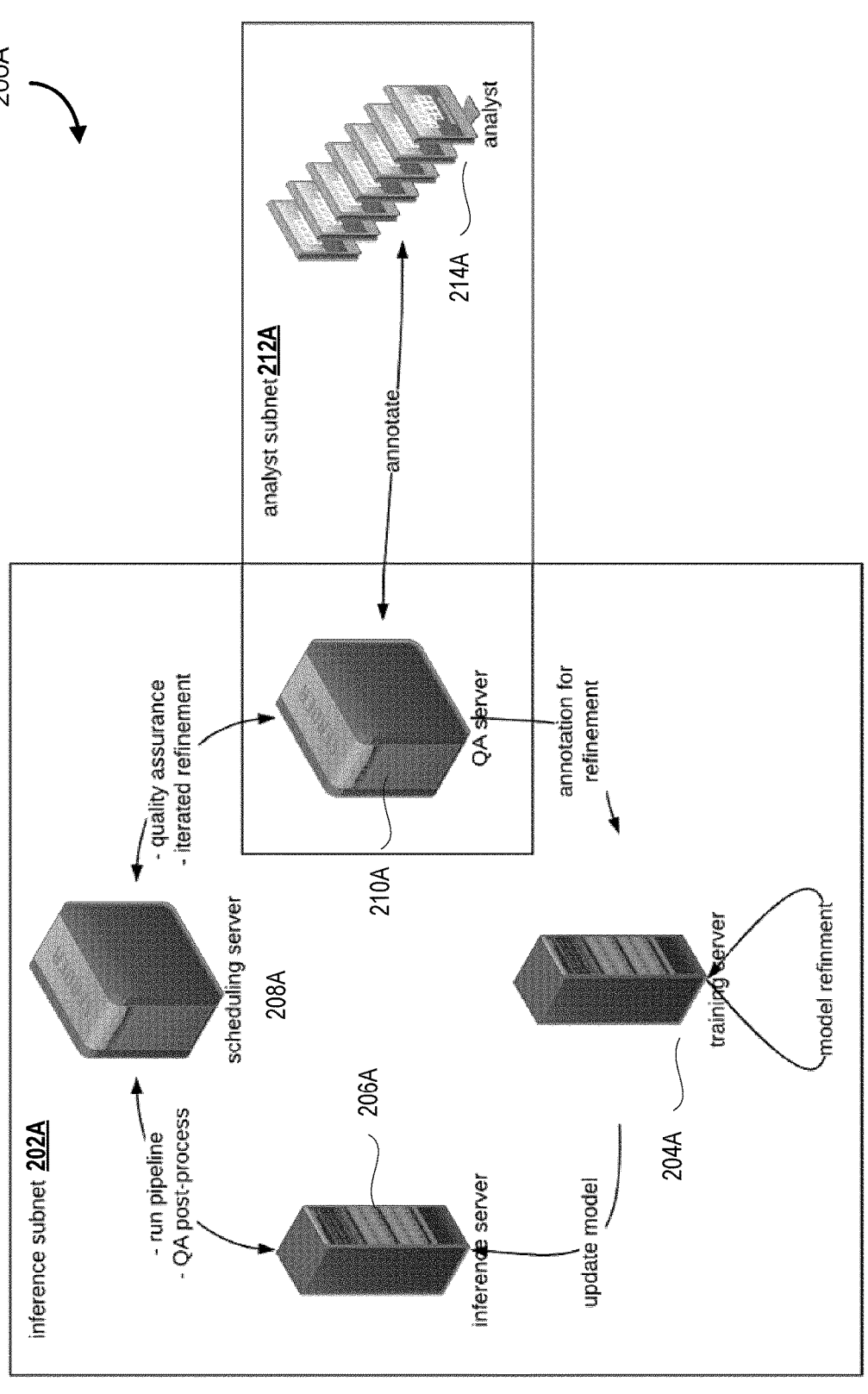
FIG. 2A is an example system for de-identifying audio or video data, according to some embodiments.

FIG. 2A is an example system for de-identifying audio or video data, according to some embodiments. The system 200A provides pipelines that take audio or videos as input and output audio videos where the aforementioned sensitive attributes have been suppressed or even completely removed. The approach consists of identifying, localizing, and tracking individuals in the operating room.

This presents challenges because input videos can be captured using wall-mounted cameras that are susceptible to occlusion. Applicants thus present approaches that combines frame-based instance segmentation with tracking across frames to minimize false-negative detection in the output video clip.

In the system shown in 200A, an inference subnet 202A operates having a training server 204A, an inference server 206A, and a scheduling server 208A. The inference subnet 202 of FIG. 2A shares a QA server 210A with analyst subnet 212A, which outputs annotated or transformed audio or video outputs to an analyst system 214A for downstream analysis.

The system 200A is an automated de-identification system is provided to process the raw captured data. The automated de-identification system utilizes specific machine learning data architectures and transforms the raw captured data into processed captured data by modifying, replacing, or obscuring various identifiable features. The processed captured data can include transformed video or audio data.

The system of 200A is configured for surgical video/audio de-identification by removing, as guided by a machine learning engine, the directly identifiable features in the video segments captured by the data in the facility (e.g., operating room). The system for de-identification may involve detecting and segmenting a region of interest based on convolutional neural networks, obscuring identifiable features based on image processing, modifying speech audio, and other components.

For each frame, these techniques are applied to surgical team members and patients in the facility, together with other objects that may indicate identifying factors. The approach concentrates, though not exclusively, on identifiable features such as face, hair, skin tone, attire, tattoos, room numbers, clocks, and monitors. A machine learning model is trained to detect objects relating to identifiable features and their corresponding visual pixels in each frame (or for audio, corresponding auditory features). For example, an intermediate output may be a tuple for each pixel indicating a confidence score and a classification, which can then be utilized for supporting the removal and/or retention steps.

De-identification transformations are utilized to modify the videos captured in the OR such that they become available for follow-up analysis without breaches of privacy.

The training server 204A is configurable with different models, such as R-FCN (region-based fully convolutional networks) for object detection, Detectron2 (detection and segmentation algorithms), YOLO v2 (a single stage real-time object detection model), SSD (single shot detector), among others. Frames of video clips are provided into the inference subnet 202A, and the system is trained using different input data sets for training and validation in attempts to automatically identify identifiable objects, such as bodies, faces, and then room-based objects or equipment (e.g., with corresponding training sets for each), and over a period of training, parameters (e.g., interconnection weightings, filters), are modified to optimize the system towards identifying the correct portions or regions of each frame of each clip to be obfuscated or otherwise de-identified.

In a first embodiment, the models utilized by the system are adapted for training to be tunable based on an additional set of input parameters, such as biasing the models towards decreasing either false positives or false negatives for a given amount of processing time or processing resources available, and in a second embodiment, the models are configured for receiving an input parameter indicative of the balance between false positives and false negatives. This input parameter, for example, could be provided in the form of an interactive interface control, such as a knob, a slider, or an input value textbox that can be used to modify the balance between different outcomes.

When the interactive interface control is utilized, the weights within the models themselves can shift or different connections can be established to bias the model outputs towards the desired control output. Being able to control the desired outcome biases can be important, as noted below, optimizing purely for false positives or false negatives could lead to issues where the system simply obfuscates the entire image (e.g., avoiding any false negatives but yielding a useless result), or doesn't blur enough (e.g., avoiding any false positives, but also yielding a similarly not very de-identified result). Rather, it can be desirable to have a system that is tuneable for a balance between false positives and false negatives. This tuning, for example, can be conducted after training, and can be conducted by modifying the models in respect of detection thresholds (e.g., softmax-outputs), or can be used to modify the loss function itself, in different embodiments.

Specifically, for the purposes of de-identification, the system can desirably be biased heavily towards reducing false negatives at the cost of increased false positives (e.g., pushing the system towards slight over-de-identification). In a variant embodiment, different trained models are sequentially used to first identify a body region (e.g., identifying everyone in the operating room), and then begin detecting their heads. In another variant embodiment, two parallel models can be used side by side for some or all of the analyses, one biased for (e.g., optimized for) reducing false positives, and one biased for (e.g., optimized for) reducing false negatives, and a mechanism to control balance between the two models may be to modify weighted contributions from normalized log its from the two models. For example, the two models may output a normalized score of 0.3 and 0.8, respectively, and in this example, a threshold score for obfuscation of a particular pixel or pixel region could be 0.5. The knob can modify a balance between the two normalized scores, by applying weights A and B to them where weights A and B add up to 1 and the balance is shifted between A and B using the knob. Biasing towards having some false positives present while ensuring that there are no false negatives, in this example, would require that A be more heavily weighted, and B less, and thus yielding an example modified score of 0.55, such that the target pixel or pixel region is obfuscated.

At this point, the head area for obfuscation can be established through the use of dynamically sized obfuscation regions that are computationally assessed by the inference subnet 202. The obfuscation regions, could, for example, be bounding boxes or other types of shapes or polygons corresponding to the region to be obfuscated in each frame, and this can be identified, for example, by processing each region of pixels (e.g., collections of pixels) or each pixels individually within the frame to generate a machine learning output, region by region or pixel by pixel, indicative of a machine learning prediction log it that can be normalized, and thresholds can be utilized as described above to modify the behavior of the system. To reduce the overall computational requirements and to yield a more smooth obfuscation experience for viewers, in some embodiments, the obfuscation, instead of specifically blurring specific pixels or pixel regions, a bounding box is established around an entire region (e.g., a square or rectangular region) where there exists some pixels or pixel regions identified as being potentially identifiable, and the entire bounding box is blurred or otherwise obfuscated. This approach can be additional useful in that it provides a greater level of comfort in reducing false negatives, as regions proximate to the identified pixel or pixel regions can often be used for re-identification or to provide context on nearby pixels.

Another variant embodiment is adapted for movement interpolation and extrapolation, where consistency between frames can be used to improve a confidence level of a particular pixel or pixel region for a given amount of finite computing resources. For example, if a surgeon is relatively stable from a position perspective in a video (e.g., standing in the same spot using a surgical apparatus), previous pixel and pixel region de-identification scores can be used in later frames and the outputs can be re-used.

While the size of the bounding box can be established as a baseline, based, for example, on the size of the object in the frame (which could depend on how big the person's head is, or how close they are to the camera), this bounding box can then be re-sized dynamically (typically enlarged). For example, if the surgeon is moving around as shown in between frames, de-identification could become more challenging. To address this challenge, the system of an embodiment that is adapted for interpolation/extrapolation can be adapted to dynamically modify or increase a size of the bounding box or obfuscation region.

Dynamically modifying or increasing the size of the bounding box can be based on observing frames bi-directionally (from a time perspective) and corresponding pixels from a particular time of reference, such that frames before and afterwards can be observed to obtain and extract a metric indicative of a potential average displacement (e.g., indicative of movement of the person in the frame within corresponding frames). For example, a surgeon could be moving around to different surgical areas (e.g., for a complicated surgery), and whenever the surgeon is moving around (as opposed to staying relatively in the same spot in the frame), the bounding box can be dynamically made larger (e.g., increasing diagonal size or number of pixels from a height or width perspective, or both), whenever it is detected that there is inconsistency in frames, which indicates that there is movement.

Based on a detected movement speed, the bounding box can be increased proportionally. For example, if the surgeon is quickly running across the frame to address an unexpected problem, the bounding box could be correspondingly much larger during this time, and reduce back to normal size when the surgeon returns to a static position. A technical benefit of such an approach is that it reduces computational complexity and may be helpful to further reduce potential false negatives, especially in the movement related frames, as the object detection is typically less able to utilize information from prior frames in reducing the total amount of computational overhead to generate an accurate result. Accordingly, if the bounding box is increased during those movement times, there is further less probability of having a missed de-identification (e.g., portion of surgeon's face showing), although at the cost of increased false positives (e.g., more innocuous regions of the frames are obfuscated).

Examples of de-identification in the medical domain are mostly limited to the anonymization of medical records. One example in the context of the operating room is by Flouty et al. [5], i.e., a deep neural network able to blur the faces on random video frames. Due to the aforementioned issues related to occlusions within operating room videos, frame-level anonymization may contain false negatives, especially if the model is applied across multiple operating rooms and multiple hospital sites.

The proposed approach described herein in some embodiments not only creates temporal tracking for the precise de-identification of individuals, but also a framework to de-identify their face, head, hair, skin-tone, genitals, and speech amongst other scene-based attributes such as the room number, equipment, clocks, etc. Silas et al discussed the effect of de-identifying operating room videos but didn't present deployable approaches for the de-identification process.

Recently, with the proliferation of deep learning, computer vision problems became much tractable using neural networks. The approaches for object detection, tracking, and entity counting in other fields (e.g., sports, surveillance, and self-driving cars) are applied in an operating room setting. From convolution neural networks (CN Ns), detecting, tracking, and segmenting images of surgical staff achieves promising results, and outperforms common baselines in crowded, high-occlusion scenarios. The outcome of these algorithms can further locate identifiable features in the OR and obscure them in the report for the client, avoiding a huge amount of manual work.

De-identifying humans (i.e., members of the surgical team and the patient) includes but is not limited to:

blurring the face (with or without surgical mask)
blurring the head and hair (with or without surgical cap)
modifying skin tone and tattoos
modifying colour of attire and other items
blurring genital regions of the patient De-identification on background scene includes but is not limited to:

blurring hospital and room number marker
blurring clocks and other equipment showing the time
blurring computer monitors (except laparoscopic monitor)
broadly obscuring the background In an embodiment, the automated de-identification system is adapted to track, in video data, objects within the field of view and visually replace them with alternate simplified graphical representations, such as pixel-based meshes, texture maps, contours, wireframes/skeletons, shaped blocks (e.g., for practitioner heads), replacement objects (e.g., cartoon bodies and block heads), blurred regions (e.g., patient genitals).

These alternate graphical representations can be tracked as the visual objects move within the field of view or beyond the field of view, or as they become obstructed.

Approaches are described herein that relate to object tracking through, for example, momentum interpolation/extrapolation such that the alternate graphical representations are adapted to be maintained despite partial obstruction, etc., with an automatic bias towards prudence in de-identification (e.g., allowing a greater emphasis on true positives, biasing the system in favor of acceptable amounts of false negatives over reducing false positives) so that the risk of potential re-identification is minimized to the extent possible.

In the momentum interpolation/extrapolation approach, while dynamically modifying bounding boxes is described earlier, it can also be implemented in a number of different ways. For example, down sampling, doing frame-wise object detection, and blurring the entire region in between over multiple frames.

Certainly, momentum allows the system to extend the blurred field around an individual as they walk. The degree of this extension is positively correlated with their speed. In Applicants' testing, this approach was very helpful for keeping an individual blurred in the context of surgical recordings.

There is a trade-off between precision and recall—and in some variations, these factors can be adjusted during the processing step.

In some embodiments, the system also obfuscates the input audio such that individuals with distinct accents and auditory characteristics are less identifiable. Audio de-identification can be used separately or together with video de-identification. Audio de-identification can include obfuscation to remove identifiable auditory characteristics (e.g., distinct accents, stammers, tone, cadence, pitch, accentuation), for example, by replacing the audio with computer-generated voices or sampled voices, etc.

Discussion and communication occur constantly an operating room. Keywords such as name, time, and hospital site should be detected and removed. Also, a person can be identified from pitch and tone, together with some other personalized frequently-used expressions. The approach to modifying speech can include audio pitch-shifting and muffling; speech recognition of the original speech followed by generation of synthetic speech from the recognized words can be applied as a more complete method to remove identifying factors in the voice itself. Segments of speech that require redaction can also simply be eliminated from the resulting audio stream.

Machine characteristics may also be replaced, for example, if there are vendor or device specific types of beeps or alert notification sounds. For the audio de-identification, in some embodiments, approaches are further described to maintain certain relevant characteristics that are useful for downstream analysis, such as periods of increased volume (e.g., yelling indicative of a situation or urgency), accentuation on various phrases, syllables, phonemes, or words (e.g., noting particular importance on those semantic objects). For example, computational models are described that allow one to speak into a neural network-based machine model, and the voice is modified to another voice. If someone is speaking, the modified voice can preserve tone of speech, sentiment, among others.

In some embodiments, approaches are described for a machine learning-based approach to interpret combinations of identifiable factors in the raw input data that can be used for potential identification of a particular procedure (e.g., heart valve replacement scheduled from 1:30 PM-2:00 PM in operating room 3) or a facility in which the procedure took place (e.g., heart valve replacement took place in hospital X).

These identifiable factors can include visual or auditory aspects such as background information, such as labelling or signage in the background indicative of which operating room (e.g., OR-3) the procedure is taking place, identifiable décor (e.g., a pamphlet on hand-cleaning procedures at hospital X), identifiable clock designs, etc. These features can be provided as part of a supervised training set of video, timeframe (e.g., timestamp), and pixel region couplet data objects, where annotated identifiable objects and their associated pixels can be used as a training set. Similarly, auditory aspects can be provided as a supervised learning set of time-stamped audio and, in some embodiments, segmented features from the audio. In the supervised learning data set, identifiable aspects are noted, such as pitch, cadence, among others.

Auditory aspects can include specific types of notification sounds, background equipment hums, periodic sounds, etc. Scene-based identifiable factors, in some embodiments, can be similarly obscured, replaced, removed, or modified. In a further embodiment, the system is adapted to track identifiable combinations and modify aspects of the combinations thereof such that it is more difficult to reverse engineer the de-identification.

The resulting media clips (video, audio) may be distributed amongst clinicians for the purpose of quality improvement, research, and education. In a variant embodiment, the system 200A is adapted for operation in real or near-real time, while in other variant embodiments, the system is adapted for operation with a particular processing time (e.g., run overnight) or target processing objective (e.g., de-identification accuracy level at least greater than 98.5%). The operational characteristics, in some embodiments, can be tweaked based on desired output, for example, by modifying hyper-parameters, such as sampling frequency, window size, a couple of graphs, among others. Processing over a period of time yields a more accurate set of models for future processing.

Real-time operation constrains the available resources and processing time, but may be useful in situations where obfuscated outputs are urgently needed. In a further variant embodiment, an initial de-identification is conducted for real or near-real time audio or video output generation, generating a first-pass audio or video output. In this embodiment, the initial de-identification is adapted for a faster generation using limited computational time and resources, and can be biased towards allowing a greater amount of false negatives to be incorporated (e.g., more pixels or visual/audio artifacts being included for de-identification). In subsequent passes that are conducted, the de-identification may be conducted repeatedly on the output to reduce the amount of false negatives, and each subsequent pass may have less negatives than prior versions.

In another variant embodiment, the conversion is one-way, and the original audio or video is deleted or encrypted after an initial de-identification pass, after a number of de-identification passes have occurred, or after a period of time has elapsed.

Figure 2B:
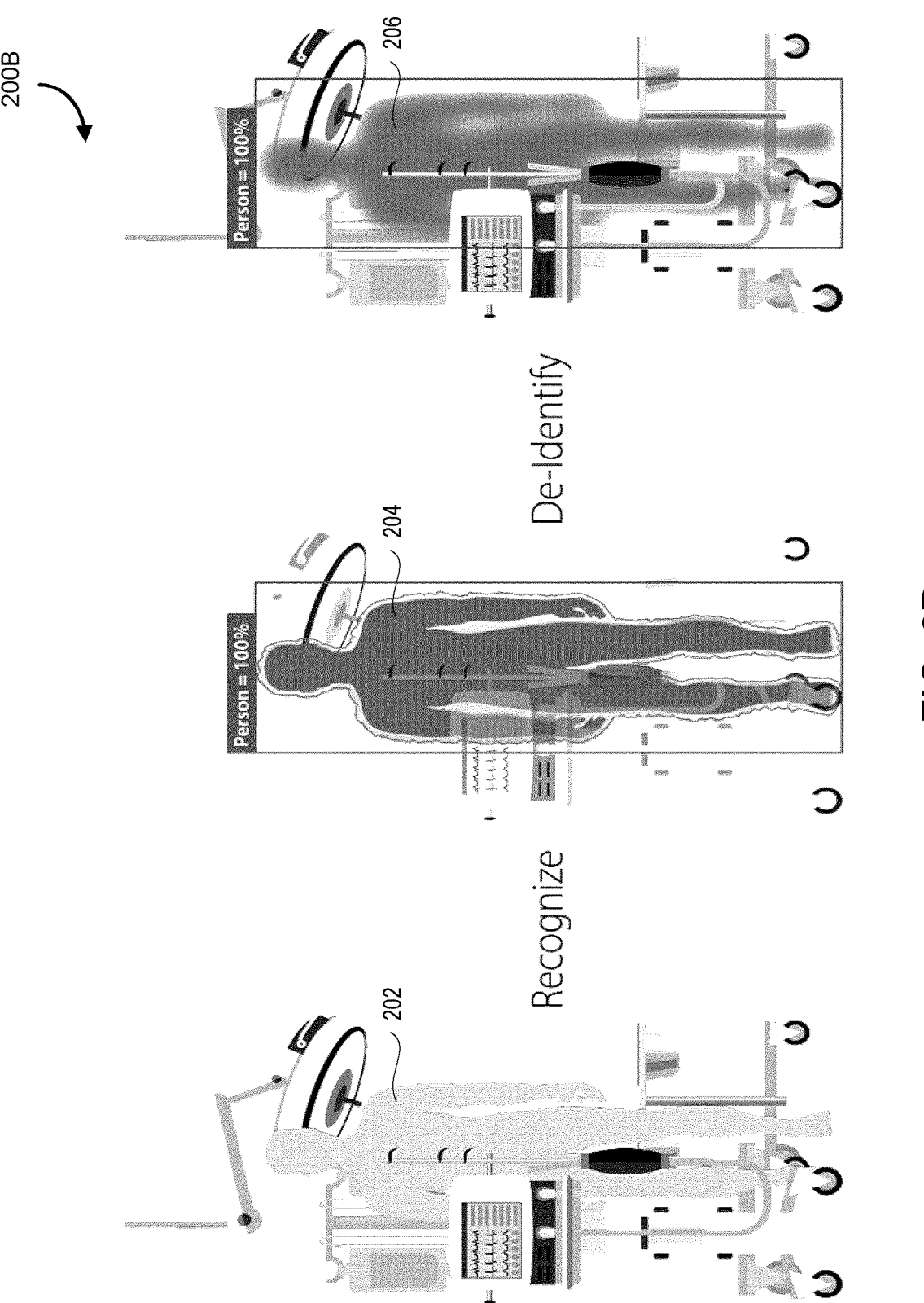
FIG. 2B is an pictorial illustration of an example output from the system, according to some embodiments, where the person is converted into a pixel cloud.

FIG. 2B is an pictorial illustration of an example output from the system, according to some embodiments, where the person is converted into a pixel cloud. In this example, an image of a person 202 is captured in a still frame of a video.

The person 202 can be identified, for example, by establishing a bounding box around the person, and the region of interest may be determined to bias the geometric dimensions of the region towards avoiding false negatives (e.g., to be more inclusive). The person is identified using, for example, a bounding box 204 which is geometrically adapted to cover the person with a high level of coverage (e.g., 100% coverage), and then used to generate the transformed/de-identified image 206. It is important to note that the area around the person in 204 has an additional margin covered by the line around the person to provide an improved level of coverage (at the cost of accuracy). While image 206 is shown as a blur, it is not necessarily a blur in all embodiments—the image 206 can include transformations such as a thematic change (cartoon-ization) of all body parts or some body parts, or changes such as conversion into a pixel "cloud" where blurring and other transformation effects are conducted based on a determined probability of identifyability associated with each pixel.

Figure 2C:
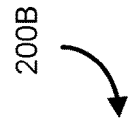
FIG. 2C is an example illustration of two undesirable examples where either recall or precision is obtained at the cost of the other.
Figure 2C:
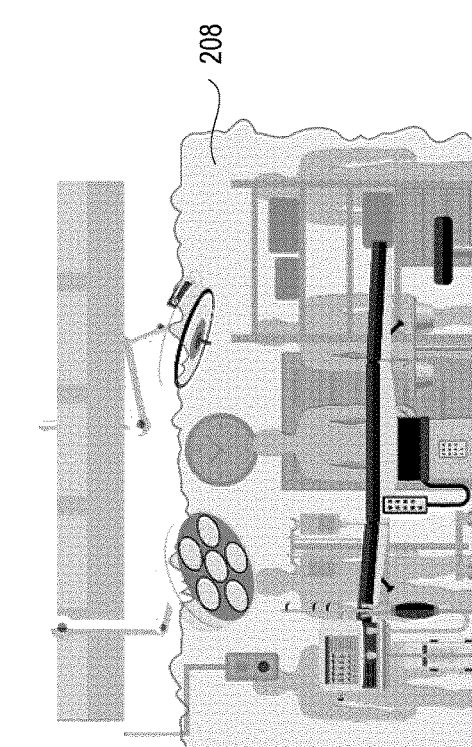

FIG. 2C is an example illustration 200C of two undesirable examples where either recall or precision is obtained at the cost of the other. In the illustration 208, the example is undesirable because while all humans are covered by the de-identification system, almost all pixels were de-identified, rendering the output useless for downstream analysis. In this example, recall was prioritized at the cost of precision. In the illustration 210, the example is undesirable because while there is high precision in respect of one human being covered by the de-identification system, other humans were completely ignored and not de-identified (perhaps because they were partially obstructed), rendering the output unsuitable for downstream analysis as there are privacy concerns present. In this example, precision was prioritized at the cost of recall.

Figure 2D:
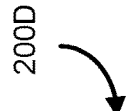
FIG. 2D is an example illustration of a desirable example where coverage is maintained over the identifiable elements with both a high level of recall and precision, according to some embodiments.
Figure 2D:
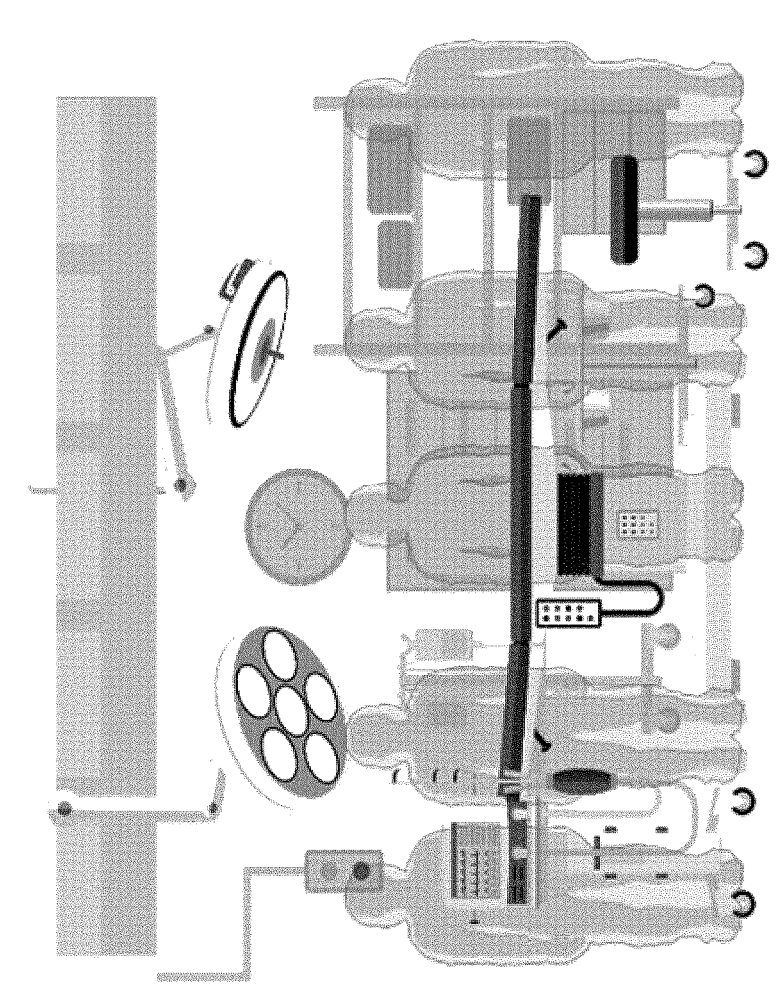

FIG. 2D is an example illustration 200D of a desirable example where coverage is maintained over the identifiable elements with both a high level of recall and precision, according to some embodiments.

The illustration 212 shows a desirable example as all humans were accurately identified, and the specific pixels of interest were detected (with some additional margin due to some uncertainty as to what pixels correspond to a human). In some embodiments, what needs to be de-identified is not necessarily the entirety of the bodies of the humans, and the precision could instead be related only to identifiable aspects, such as heads, faces/headgear, skin color, tattoos, identifiable marks on clothing, among others.

Experimental Validation

The MS-COCO (Microsoft Common Objects in Context) dataset is a large-scale computer vision dataset developed for tasks like object detection and instance segmentation. Example models for head detection and body segmentation in de-identification are pre-trained on the COCO dataset and utilized for testing some embodiments described herein.

The MS-COCO dataset provides general features of images, like colour, texture, pattern, etc. However, the operating room/medical facility scenario is unique compared to common objects in general surroundings. The deep learning model can be confused with highly occluded objects with similar attire. Also, visible features of humans such as heads and skeletons are blocked by the surgical mask, cap, and gown.

To improve the effectiveness of computer vision models on this challenge, Applicants sampled 3308 images from three partner hospitals with 9 operations each and annotated the ground truth of head detection and body segmentation for both members of the surgical team and patient. Models trained specifically on this operating room video dataset was found to achieve better results on evaluation metrics than ones ones pre-trained on MS-COCO or similar public datasets.

Methods

Specific techniques described below to aid in achieving de-identification over video and audio are described in various embodiments. Approaches for model switching, cooperation, and system management are also described.

Room Video Obfuscation Techniques

Head

The head can be an important feature to remove when identifying members of the surgical team and patient. Therefore, a head can be blurred together with the surgical cap and mask. This can be achieved by the following steps: head detection, head tracking, and head blurring.

For head detection, the first step is to obtain a probability (or pseudo-probability) distribution over possible head location. Object detection can be accomplished, for example, by utilizing convolutional neural network (CNN) approaches for object detection. A CNN can extract low-level features of images and detect the object by bounding boxes.

In an example embodiment, the system 200A using inference subnet 202A can be configured to apply ResNet [7] with an FPN (feature pyramid network) [9]. The selected ResNet has visual representation capabilities with a depth of up to 152 layers, and reduces a required effort to optimize by the residual structure. The inference subnet 202A, through a data model architecture takes RGB images as input, passes through the region proposal network (RPN) to generate initial proposals, extracts image features by residual CNN, and predicts object locations as in Faster R-CNN [15].

Also, the apparent size of objects in a medical procedure environment (e.g., operating room) may change drastically due to the camera location and object motion, and this can invalidate ResNet on small objects, especially when surgeons or nurses are far from the cameras. Accordingly, in some embodiments, the inference subnet 202A is configured to apply FPN to extract image features on different scales and make finer detections. In experimentation, the ResNet-FPN model was pre-trained on the COCO dataset and fine-tuned on the operating room room video dataset.

To achieve high performance, head detection, in some embodiments, is only run on sampled frames (e.g., sampled per 5 frames), so that intervening frames need to be smoothed or interpolated. In this example embodiment, the inference subnet 202A is configured to use momentum-based interpolation, which is smoother and closer to the real trajectory compared to simply copying bounding boxes from closest frame. Momentum based interpolation/extrapolation allows the system to extend the blurred field around an individual as they walk. The degree of this extension is positively correlated with their speed. This can be crucial in keeping an individual blurred.

Momentum-based interpolation includes first detecting objects on key frames, then using an intersection over union tracker engine to identify the same object on the consecutive key frames. For these frames, the displacement of four anchor points of a bounding box [top left, top right, bottom left, bottom right] can be determined, and the edge momentum can thus be obtained by averaging displacement and calculate the coordinates of anchor points on non-key frames. The edge momentum can then be used to add smoothing at the beginning and end of each track.

Figure 3A:
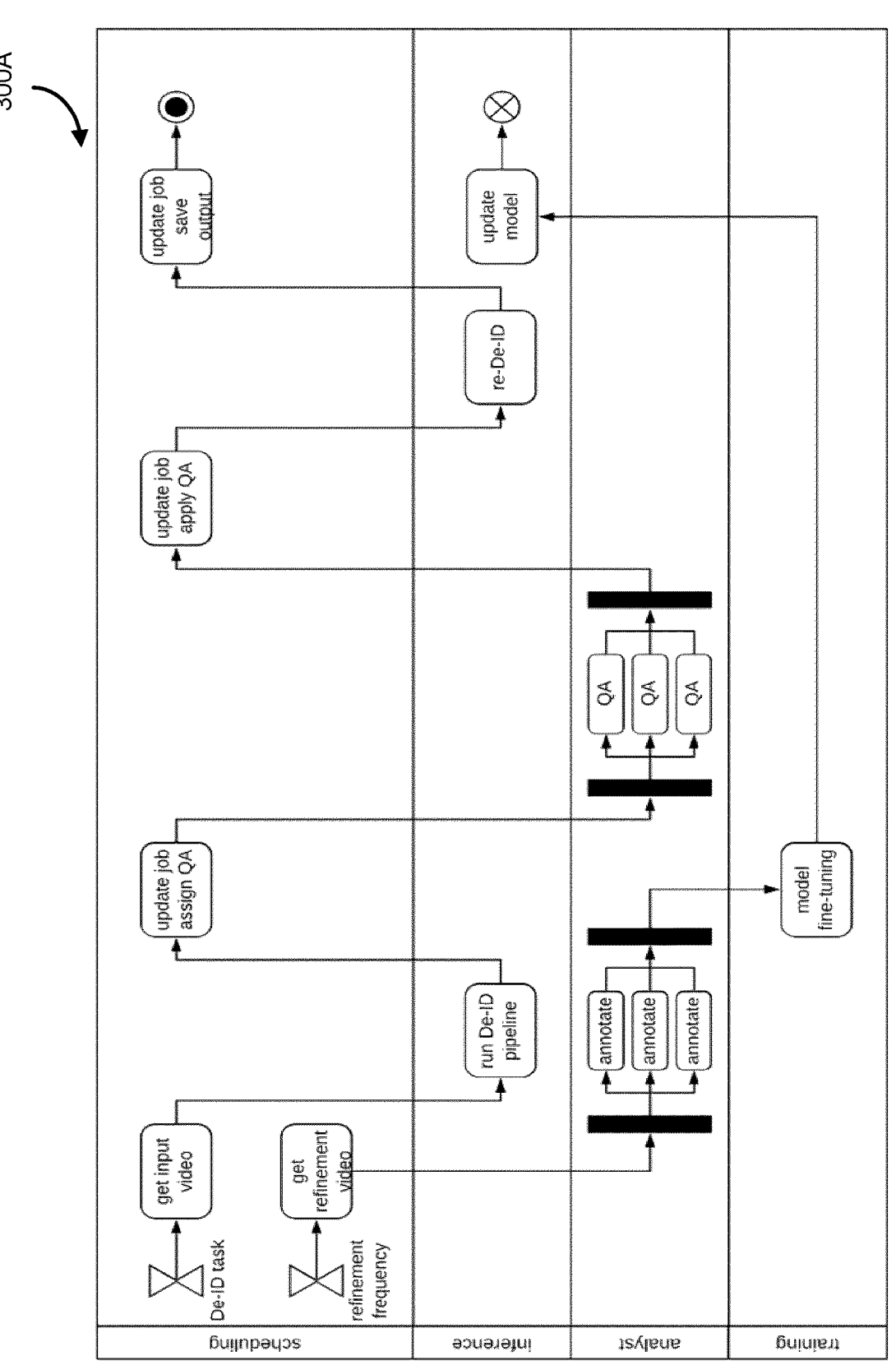
FIG. 3A is an example pipeline process for quality control, according to some embodiments.
Figure 3B:
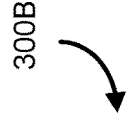
FIG. 3B is an example illustration of an example, drawing of a intersection over union tracker, and predictions across a set of frames used for momentum-based interpolation, according to some embodiments.
Figure 3B:
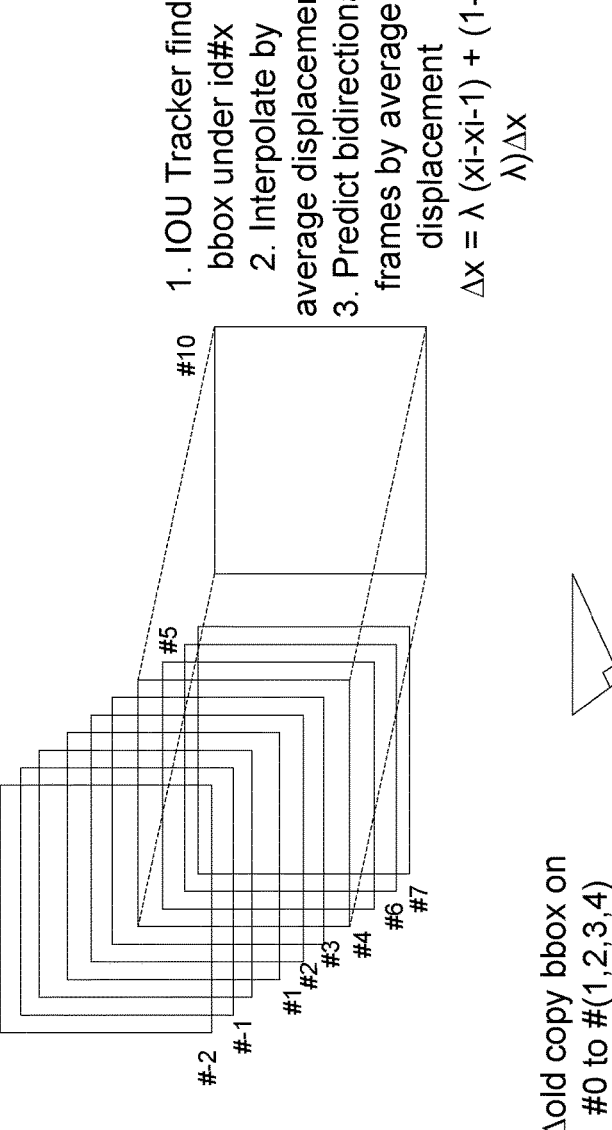

FIG. 3B is an example illustration 300B showing the drawing of a intersection over union tracker, and predictions across a set of frames used for momentum-based interpolation, according to some embodiments.

Head tracking can help to find the same detected object in consecutive frames, and momentum can be additionally calculated as the average displacement of the same bounding box between frames. Also, false negatives usually happen at the beginning or end of each trajectory; using the momentum to grow the trajectory at both sides can help correct for this, to some extent.

Tracking solutions [4] can be transferred to medical procedure (operating room) scenarios. An approach, according to an embodiment, is to conduct machine vision analysis on existing bounding boxes, find a temporal relationship, and match the boxes of the same person. According to the operating room example scenario, some objects move much less than others. In these situations, the simple (but fast) IOU Tracker [3] may be sufficient for production requirements.

The principle of the IOU Tracker is that bounding boxes of the same object on consecutive frames should have a greater coverage compared to other groups.

IoU (intersection-over-union) is a measurement of overlapping areas, defined as:

$$IOU_{a,b} = \frac{\text{Area}_a \cap \text{Area}_b}{\text{Area}_a \cup \text{Area}_b}$$

After the head location is represented as bounding boxes on each frame, heads can be blurred, for example, by applying OpenCV based average filtering. This blurring approach can be fast and convenient.

Body

It is possible to identity someone from aspects of their bodily appearance, like skin color, tattoos, preferred attire, or special accessories, even the body shape. Co-workers familiar with an individual could make a confident guess as to their identity. Accordingly, a goal of 'body appearance modification' is to cause every person in the medical procedure room (e.g., operating room) look as similar as possible. This can be achieved by applying the following steps: body segmentation, body obfuscation.

In an embodiment, the system is configured to first establish a pixel-by-pixel contour around a particular region indicative of the person (or objects as described in other sections), and a label can be ascribed (e.g., in the context of an object).

First, body segmentation is applied by inference subnet 202A whereby the inference subnet 202A is configured to locate where the body is in the frame (e.g., a centroid, corresponding pixels).

Compared to the head, the shape of the body varies much more and can be easily occluded partly. In some embodiments, an instance segmentation model can be applied on the body by finding all pixels belonging to one instance. Here, a possible approach is to use ResNet with FPN, as for head detection.

The model receives RGB images as input, passes the input through the region proposal network (RPN) to generate initial proposals, extracts image features by residual CNN, and predicts instance location as in Mask R-CNN [6]. The output of the instance region can be represented as a polygon mask. In experimentation, the ResNet-FPN model was pre-trained on the COCO dataset and fine-tuned on the operating room video video dataset. An example of a polygon mask is provided in a 2018 paper entitled Mask R-CNN, from Kaiming He et al.

For body obfuscation, the region of the image, associated with the instance segmentation masks, can also be transformed by effectively thickening major edges and features. This transformation results in the region losing some of its realism, resulting in a somewhat 'cartoonish' appearance.

The reduction in the realism of certain regions removes patterns on the individual's identity (such as tattoos, distinctive marks, etc.).

To achieve this, the inference subnet 202A is configured to find edges of each body instance under the region of segmentation mask, using, for example, an adaptive threshold and then generate obfuscation representations based on the edges generated and replace the pixels of body.

Another potential objective of the de-identification module is to decrease the discernibility of individuals. To this end, the instance segmentation masks aim to encapsulate the body to such an extent that pixels associated with the individual's skin are transformed into a different color. The color values of pixels under the body mask can, for example, be re-scaled.

Facility Objects and Décor

For detecting objects and décor, a similar model for other types of object detection (bodies, heads, can be used, but separate neural networks can be used to be trained such that they maintain different internal representations for different objects, which they learn during supervised training.

An operating room may include various objects from which a third party can identify detailed operation information. These can be inferred from operating room number markers on the wall, clocks, monitors, etc. Then, the identity of patients or surgical team members is obvious if familiar with the hospital.

A possible solution is to extend the existing head detection model, and turn it to a multi-class object detection model on surgical team head, patient head, monitor, clock, OR number, etc. and then the object blurring is applied similarly to head blurring. Training, for example, can be conducted to extend the model to multi-class object detection using a balanced dataset on each objects.

Genital Region

During the preparation and patient transferring after the surgery, the genital region of the patient is usually visible to the cameras. This may not be acceptable in all scenarios. These parts need to be detected and blurred.

This can be achieved as an add-on feature in body segmentation: instance segmentation can be fine-tuned on a labeled genital region and blurring is applied; other parts of the body may, in some embodiments, be kept the same or similar. In some embodiments, there may be further obfuscation on patients' body for identifying characteristics, such as the skin tone, tattoos, etc.

For detecting genitals, a similar model for other types of object detection (bodies, heads, can be used, but separate neural networks can be used to be trained such that they maintain different internal representations for different objects, which they learn during supervised training. In another embodiment, the genital region can simply be obtained in relation to skeletonization models and tracked body part positioning, as typically, since all persons keep their genitals in the same area relative to other body parts, and identifying the various body parts allows a rough estimation of a region in which genitals may be present. For that region, pixels or pixel regions can have prediction values adjusted accordingly such that the genitals are obfuscated.

Overall Frame Obscuration

As in the scenario of choosing to retain information, most of the image is obscured or modified unless specifically requested. In this scenario, most of the medical procedure facility (e.g., operating room) room video needs to be changed. There are several principles to consider:

level of de-identification: the technique applied should ensure that no information is left available to identify the medical procedure facility (e.g., operating room) or people (i.e., the surgical team and patient); this level may be flexibly changed;

context: the technique should keep the context of the input image that is useful for subsequent surgical analysis, such as the overall medical procedure facility (e.g., operating room) setting, human traffic patterns, coordination behaviors, surgical technical/non-technical skills, movements disobeying protocols, etc.;

speed: the technique applied should be fast, as most of the image can be changed; and decomposability: it is better that the modification can be decomposed into several semantic levels, such as dealing with the background and foreground separately, or high-traffic and low-traffic; this aids in configuration of the tool and can control extra post-processing.

There are several potential methods of overall frame obfuscation with different behaviors. These can be applied, for example, per request from various facilities.

Overall Blurring

Overall blurring can be applied by using averaging blurring approaches to to all the pixels in a frame. This method can have extremely fast blurring speed and identifying features can be thoroughly removed. However, the approach may have difficulty in maintaining context. Overall blurring is an option, but a challenge is that it may blur every pixel and make the whole image de-identified, at the cost of losing all or almost all of the information.

Edge-Based Obfuscation

Edge-based obfuscation can be achieved by applying an adaptive threshold to all the pixels in the frame. The speed of obfuscation is fast, the obfuscation level can be modified by parameter a and many context details for surgical analysis can be kept. However, sometimes features such as the head are difficult to de-identify thoroughly and foreground/background separation is a sensible alternative.

Edge-based obfuscation can be applied on a body polygon mask retrieved by instance segmentation model, and can be applied at most times. Situations where edge-based obfuscation is not applied includes situations where there is no need for body obfuscation or when the system needs an extremely high running speed.

Style Transfer

Style transferring applies CNNs to modify the style of any input image to be similar to another reference style image, but keep the content as consistent as possible.

Figure 6:
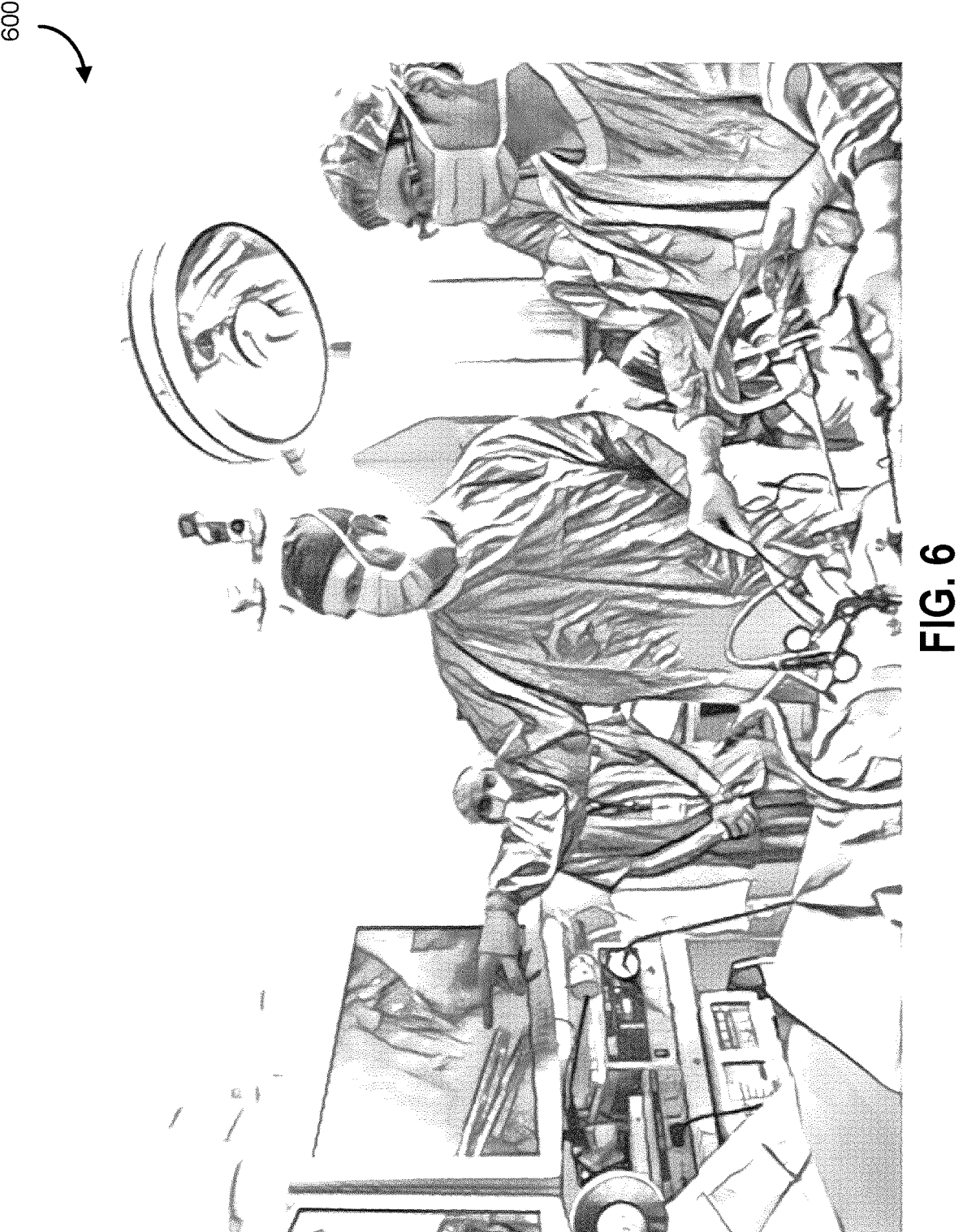
FIG. 6 is a reference example of a style transfer, according to some embodiments.

Style transferring, in an example, can be used to convert an image to a cartoon style, among others. FIG. 6 is a reference example of a style transfer, according to some embodiments. In FIG. 6, illustration 600 shows a frame that has been partially converted into a cartoon. This can change the style representation of the image and make it hard to identify. Style transfer applications such as https://github-.com/lengstrom/fast-style-transferFast Style Transfer in TensorFlow used CNNs to extract content representation from the input image and style representation from the style reference image, and generate a new image based on these two representations.

Compared to overall blurring and edge-based obfuscation, style transfer can generate various representation while keeping context details for surgical analysis, also its obfuscation level can be modified by a parameter. Also, it is slower than the methods above, and its aesthetic output is not as directly controllable.

Room Video ROI Retaining Techniques

One principle of de-identification is to avoid the impact on surgical analysis. Some ROI (Region of Interest) in the frame should not be changed or should maintained similar to the original image as much as possible, such as surgeon/nurse arm and hand, patient body, laparoscopic monitor, etc.

Several methods are proposed below to keep information in different levels, and this may change for different sites and different surgical analysis purposes.

Skeletonization

It is important to evaluate surgeons' technical/non-technical skill by fine and coarse movement, especially with the arm and hand. Some rule-breaking behavior can be identified from the pose.

Skeletonization approaches can be used to decompose the human body into the shape of several key points, and edges between points can show different parts of a skeleton. From this, the movement of these points carry semantic content and can be used for further analysis. Also, skeletons can show the direction in which each person faces, which can be used to analyze attention, roles, or cooperation evaluation.

In implementation, the system can be adapted to utilize ResNet with FPN. The model takes RGB images as input, passes through the region proposal network (RPN) to generate initial proposals, extracts image features by residual CNN, and predicts instance location as in Mask R-CNN [6]. The output of the key points is represented as a list of point coordinates with a certain order. System 200A can be configured to apply a model from https://arxiv.org/pdf/1703.06870.pdf, a detectron which can be pre-trained on the COCO dataset. The skeleton can be placed on the blurred, obfuscated, or otherwise style-transferred images to show human-related information. The skeleton tracking can be utilized in situations where it is useful to know about people's shape but not other details, as additional information will be lost relative to obfuscation.

As described above, genital obfuscation can be done alongside skeletonization by identifying where on the skeleton genitals would typically be located (e.g., below the trunk of the abdomen or between identified leg body parts), and the region can automatically assigned prediction score weightings to automatically bias the ultimate transformed outputs towards obfuscating the genitals (e.g., for a small square region confidently identified in the skeletonization as the sub-abdomen area where the legs meet or the pelvis would be, increase the prediction scores by 0.25 such that the system is heavily biased towards obfuscating the pixels or the pixel regions, or to implement a bounding box for obfuscating the entire area).

A benefit of this type of genital obfuscation by the system is that there is be a reduced need or no need for a human reviewer to see images of the sensitive regions, such as genitals, in generating the de-identified output.

DensePose

Skeletons can only represent limited information and can therefore be a drawback for surgical analysis. DensePose [1]

is a compromise between pose estimation and instance segmentation. DensePose builds a spatial representation in the format of surface coordinates on each part of the body by only RGB input. Having the coordinates on each part of the body, the system can normalize the depiction of humans in the scene to some predefined template.

Relative to skeletonization approaches which transform images of people into stick figures images, DensePose turns people into more amorphous collections of body parts.

DensePose can segment each person in the image, and outputs finer segments as part of the body. Inside each part, the system builds independent coordinates and can use it to modify the visualization color. Also, the coordinates inside each part can be related to SMPL (A Skinned Multi-Person Linear Model) [11]. The person in the image can then be replaced with a mesh-shaped texture and normalized.

Multi-Class Segmentation

An instance segmentation model can find all pixels belonging to one instance. Here, the system utilizes a ResNet with FPN architecture, in some embodiments. The model takes RGB images as input, passes through the region proposal network (RPN) to generate initial proposals, extracts image features by residual CNN, and predicts instance location as in Mask R-CNN [6]. The output of the instance region is represented as a polygon mask. The approach provided in https://arxiv.org/pdf/1703.06870.pdf provides Mask R-CNN instance segmentation models pre-trained on COCO dataset. The system can be configured for fine-tuning on operating room data to obtain a better result. Then, the system can apply different techniques such as blurring or obfuscation on different classes of objects.

Hierarchical Model Switching

While there are many models to be applied on medical procedure facility (e.g., operating room) room video, a challenge arises as designed for different purposes, they may cause conflicts among each other. For example, a modified hand covering a blurred head may cause a conflict. From the goal of removing identifying features and keeping anonymous, the model should take effect with different priorities as shown in FIG. 1.

When conflicts occur (like between keeping or blurring a segment), components on the top of the hierarchy should have higher precedence, and components at lower levels should be over-ruled. If the changing of two components has no theoretical conflicts (such as body obfuscation and skeleton retaining), over-ruling should not be applied unless there is a specific exception. The hierarchy provided in the form of instructions and rules can be used to apply various rules that enable over-ruling certain outputs and/or aspects of the model (e.g., over-ruling the model to enforce privacy constraints and requirements.

The hierarchy can be implemented, for example, as a series of weightings that applied to the particular regions or pixel regions, such that head blurring, genital blurring, have increased importance in an output prediction that is ultimately limited by available computational resources and

Laparoscopic Video Techniques

Laparoscopic videos may also contain sensitive data that may be used to identify individuals. During the cleaning and insertion of the camera into the body, the faces of the operating surgeons and portions of the patient may be captured by the camera since the camera is not turned off at any point during the surgery.

To ensure that none of this sensitive data is captured, inference subnet 202A can be configured to train a neural network model for the binary classification task of differentiating between frames that are inside the body and those that are outside of the body. In this example, all of the frames that are outside the body can be blurred or completely removed from the output video clip, thus preserving the context required for analyzing the video without any sensitive data.

A ResNet50 [7] model can be trained for this task with the purpose of learning a set of high-level representations for discriminating between external view frames which usually consist of an individual, a face, or surgical equipment, and internal view frames consisting of tissue and surgical instruments. By training this model on a large dataset of frames, each annotated with a binary label, an experimental model was able to achieve 98% accuracy, 97% precision, and 97% recall. The trained model yields a throughput of 100 frames per second during inference. The throughput of the model may be increased further by using a smaller set of frames or a smaller model such as ResNet18.

Audio Techniques

Audio de-identification is important, as personal identity can be inferred from one's accent, tone, pitch, etc. As a quick attempt, a naive approach can include the application of pitch shifting. However, this technique is reversible and can be inverted by simple parameter tuning. An irreversible method to de-identify the speech audio should nevertheless keep its content as identical as possible, for subsequent analysis. Also, some words mentioned in the speech can be identifying to the team or patient. These need to be spotted and removed for thorough de-identification.

Pitch distortion can minimize the personal features in speech can make it hard to tell who the speaker is directly. In the current version, this is implemented in the following steps:

Synchronous Overlap Add: shift the pitch up or down to change the personal feature of speaking. As all the audio is maintained, just (as the name suggests) overlapped to various degrees to change pitch. Thus, most voice characteristics are maintained, such as loudness, accents, intonation, etc.

Low pass filter: squeezing the sounds with a bandpass filter, which has its own distortion effect. The low pass filter removes high-frequency components of speech, which can result in a muffled-like sound, in some embodiments. When using a low-pass filter, low frequencies are maintained, along with and and all vocal characteristics.

Keywords in the medical procedure facility (e.g., operating room) speech audio that can lead back to operation information or personal identity should be removed, in some embodiments. These include audio words can include patient name, surgical staff name, medical procedure facility (e.g., operating room) name and number, hospital name, time, etc.

Keyword spotting can be broadly grouped into two approaches: keyword-filler and LCVSR methods. Keyword filler methods use one model for each keyword, and one model for filler for each non-keyword. LCVSR attempts to automatically transcribe all the speech first, then searches for keywords.

Given the difficulty of automatically transcribing the entirety of a surgical procedure, this project will approach keyword spotting using the keyword-filler method. A data-driven and clinically-refined approach will be used to develop a set of useful words for keyword spotting for various downstream tasks. Challenges include the high SNR in the audio and the anchoring of keywords to onset and offset times. In some embodiments, system 200A is configured to identify the key words as in [12]:

Find the keyword that best matches the utterance segment using dynamic time warping (DTVV);

Find the version of the spoken keyword that best matches the utterance segment;

Repeat for each keyword;

Given an utterance U, the resulting vector is the target containing normalized probability scores indicating the presence of each keyword found in above steps; and Train each utterance, target pair in a CNN.

Moreover, system 200A can be configured, in some embodiments, to apply named entity recognition on speech transcripts to find meaningful nouns, pronouns, and verbs instead of creating a list of keywords.

In addition to pitch shifting and muffling, several other audio processing techniques can be used to de-identify a voice. These include adding distortion, reverb or echo, pulse modulation (robot), different filters, and combinations of these techniques to generate various effects.

Speech Recognition & Synthesis

One method to de-identify speech audio is to generate text from the speech, and then synthesize speech with the resulting transcription.

Speech Recognition

Speech recognition is broadly split into three steps: audio feature extraction, acoustic models, and language models. The audio features transform audio from time domain representations to a more meaningful frequency representation of the audio. Common audio features include Mel frequency cepstral coefficients (MFCCs), filterbank energies (fbanks), and feature-space maximum likelihood linear regression (fMLLR) [14]. Common acoustic models are based on either Hidden Markov Models (HMMs), neural networks, or both (chain models). Language models map a series of graphemes to words and sentences. They generally contain a dictionary of words and their frequencies in the language.

The main challenges for speech recognition in the medical procedure facility (e.g., operating room) is in the acoustic model and language model. The acoustics of an operating room are unique and due to the dynamic environment of the medical procedure facility (e.g., operating room) there is a high amount of noise and sound events. The signal in an medical procedure facility (e.g., operating room) recording is also usually weak, due to speakers being muffled from surgical masks and being far away from the microphones.

After obtaining transcriptions from speech recognition, system 200A is, in some embodiments configured to synthesize speech from the transcription, thus de-identifying the speaker by removing the original voice and replacing it with a synthesized voice. MeIGAN is a speech audio synthesis model provided by Descript (Lyrebird) and MILA under the MIT license. Other effective speech synthesis engines are Tacotron2 [16] and Waveglow [13]. Tacotron2 uses a recurrent sequence-to-sequence neural network to generate audio features directly from text. Following this, they use a modified Wavenet and GLOW flow-based neural network called Waveglow to generate speech.

In SV2TTS [8] a desired voice can be made to say a certain line of text by encoding a short amount of the desired speaker's voice. The neural network is based an attention and an encoder-decoder architecture.

Speech Conversion Another approach for audio de-identification is to converse the speech end-to-end, without a middle ware like transcription.

Parrotron [2] is and end-to-end speech-to-speech conversion model which takes speech audio as input and outputs the audio with a fixed accent and consistent articulation and prosody. This model is composed of an encoder, a spectrogram and phoneme decoders, followed by a vocoder to synthesize a time-domain waveform.

In a variant embodiment, neural voice puppetry techniques can be utilized based on an audio track and an image to generate a video of someone speaking. In this embodiment, audio is to perform a more realistic video de-identification. Given any face and an audio, the system is adapted to make the face appear as if it is speaking the contents of the audio.

In some embodiments, the system could, for example, change a person's face to be another face (for example, a celebrity) while having the face appear as if it is speaking what was originally spoken. The effect would be a de-identified face (because it is a different face than the original speaker) but it would appear as if they are speaking naturally.

System Management

As a production-level solution, de-identification approaches would have an capability to schedule, execute, and check the job running automatically. An outbound service may be adapted to provide input videos and a list of components needed to run.

An example quality assurance workflow is shown as FIG. 3A. FIG. 3A is an example pipeline process for quality control, according to some embodiments. In this example, a de-identification pipeline can be conducted based whenever a computer implemented de-identification task is initiated.

After the automatic de-identification task is completed, the task can be assigned to a quality assurance module, which, in some embodiments, could include manual tasks conducted by human reviewers, or in some embodiments, could include a separate set of machine learning models adapted to quality control to detect if any pixels or audio features are identifiable for any particular individuals or facility.

A job scheduling service may be utilized to initiate a number of de-identification data process tasks. These data process tasks can include, for example:

pre-processing: gather input video; analyze required components; load required models;

GPU allocation: find available GPU if exists; lock GPU device for pipeline;

pipeline execution: execute pipeline on allocated GPU and monitor status;

job status update: gather output and log for the finished job; unlock allocated GPU device; and post-processing: send to system feature Quality Assurance if succeeds;

reschedule if fails.

As described in various embodiments, de-identification can have many use cases. A target is that de-identified videos ideally have 100% recall and perfect modification on outputs. So, for this purpose, system 200A can be adapted to use surgical analysts for final quality control on the model outputs, mainly for detecting bounding boxes, segmentation masks, and transcription. The de-identification task-flow may include the following steps, as shown in flowchart 300A of FIG. 3A:

create QA task: respond to a QA request from a scheduling server; create QA task for detection and segmentation on Scalabel; copy required files to sharing folder;

notification: create QA task on task management web page and assign to the analyst; send a notification to analyst;

retrieve annotation: listen and wait for the task completed on task management web page; download all annotations;

re-De-ID: re-run blurring, obfuscation, and color-changing by given annotation in the same way as the original process; and send back: collect all QA outputs and send back to the scheduling server.

Evaluation

To evaluate the effectiveness of head detection and blurring, system 200A was configured to pick 5-second video clips from 3 different hospital sites. All of examples are real surgeries with visible patients and surgical team members. Each clip is annotated with two detection type 'Head' (head of surgical team) and 'Patient' (head of patient).

Considering the problem definition and method of detection, The following changes were made to the definition to determining of recall and precision in relation to the meaning of coverage:

true positive coverage rate: Applicants define pixel percentage for each frame such as 0.8 (not 1 if over threshold as traditional recall), and then average on frames; and positive predictive coverage rate: Applicants define pixel percentage for each frame such as 0.8 (not 1 if over threshold as traditional recall), and then average on frames.

Accordingly, true positive coverage rate=0.8 would not mean 10% of objects are missed, but rather, a satisfactory result is that 90% of head pixels are covered by the approach.

Results

Result shown in Table 1 are provided under following settings:

IOU (Intersection Over Union): 0.5 sampling rate: 5 (detect per 5 frames and interpolate in-between)

TABLE 1

| | Head blurring result | |
|---|---|---|
| Site | True positive coverage rate | Positive predictive coverage rate |
| Site 1 | 0.75110288 | 0.869994 |
| Site 2 | 0.85910304 | 0.79496963 |
| Site 3 | 0.78280166 | 0.90638944 |

Laparoscopic Video Camera View Classification

Evaluation of the laparoscopic de-identification model was completed using 18 test video clips. Frames were extracted from these video clips and they were processed through the model. Each frame was classified as being either an internal view frame or an external view frame. All frames that are external are blurred or in some cases, completely removed to ensure that surgeon/patients are de-identified.

Precision and recall metrics for this classifier are presented in Table 2.

TABLE 2

| Laparoscopic de-identification results | | |
|---|---|---|
| Class | Precision | Recall |
| Internal view | 0.95 | 1.00 |
| External view | 1.00 | 0.96 |

Figure 3C:
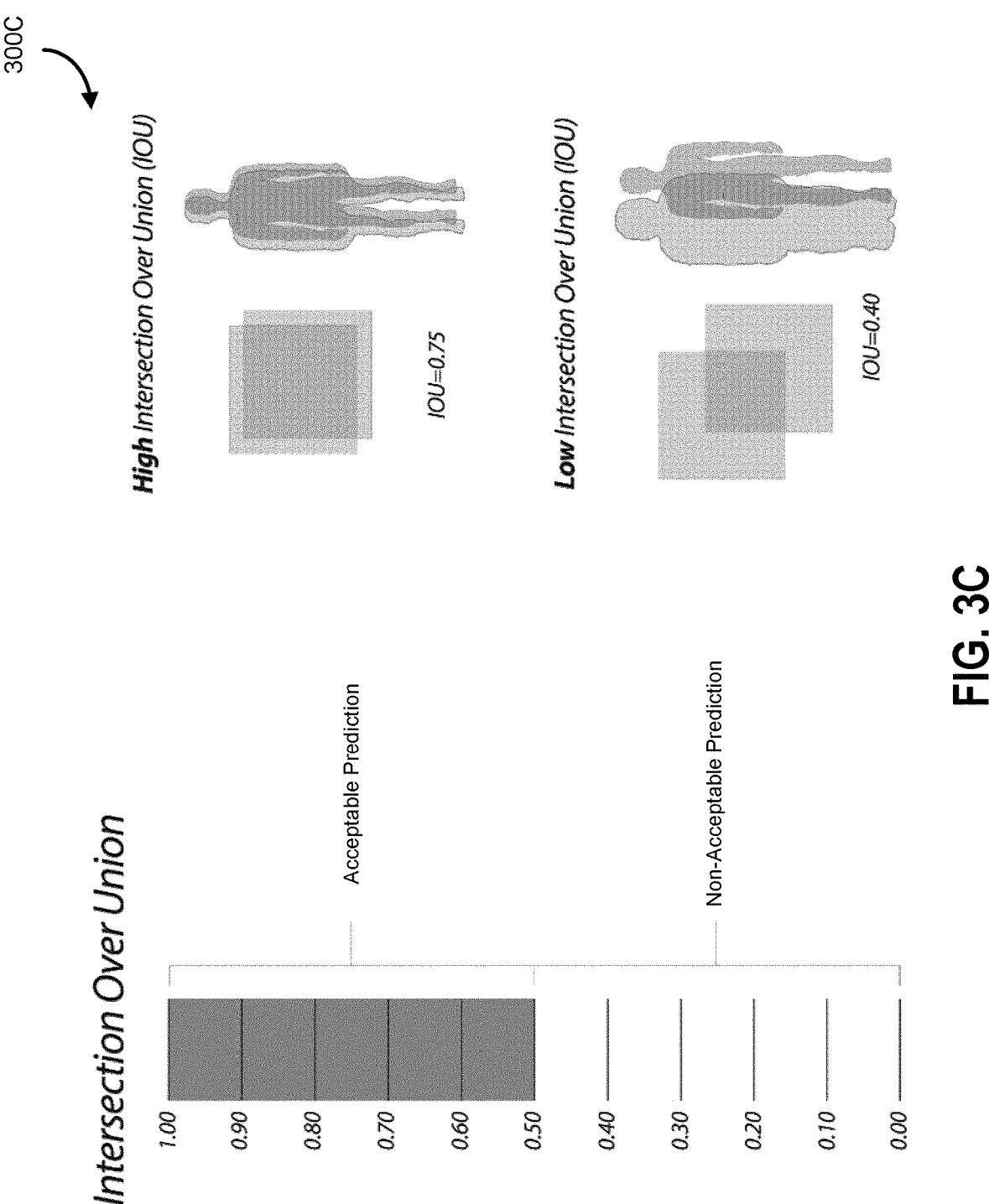
FIG. 3C is a set of illustrations noting an example threshold between an acceptable prediction and a non-acceptable prediction as determined using intersection of union techniques, according to some embodiments.

FIG. 3C is a set of illustrations 300C noting an example threshold between an acceptable prediction and a non-acceptable prediction as determined using intersection of union techniques, according to some embodiments.

As shown in FIG. 3C, there can be a range of intersections over union where the prediction is acceptable, and where it is not acceptable. In this example, a threshold of 0.50 (50%) is shown, but the threshold can be varied. The use of intersection of union as an analytical tool to determine acceptability is useful as it can track how tight the coverage is in respect to the actual person.

In this example, the larger outline is mapped to the underlying human image (e.g., as noted by a reviewer or a secondary machine learning model) to establish how well the system was able to cover the underlying human image. In the top example, an example of a desirable amount of overlap is shown (IOU=0.75), where there is good overlap relative to the underlying pixels of the human. In the lower example, an example of an undesirable amount of overlap is shown (IOU=0.45).

Intersection over union is a useful technique for tracking accuracy, especially over durations of time. However, a drawback with using intersection over union occurs where there is no intersection, and in these situations, the system can be configured to utilize dynamic time warping techniques for measurement instead or in conjunction with intersection over union.

Figure 3D:
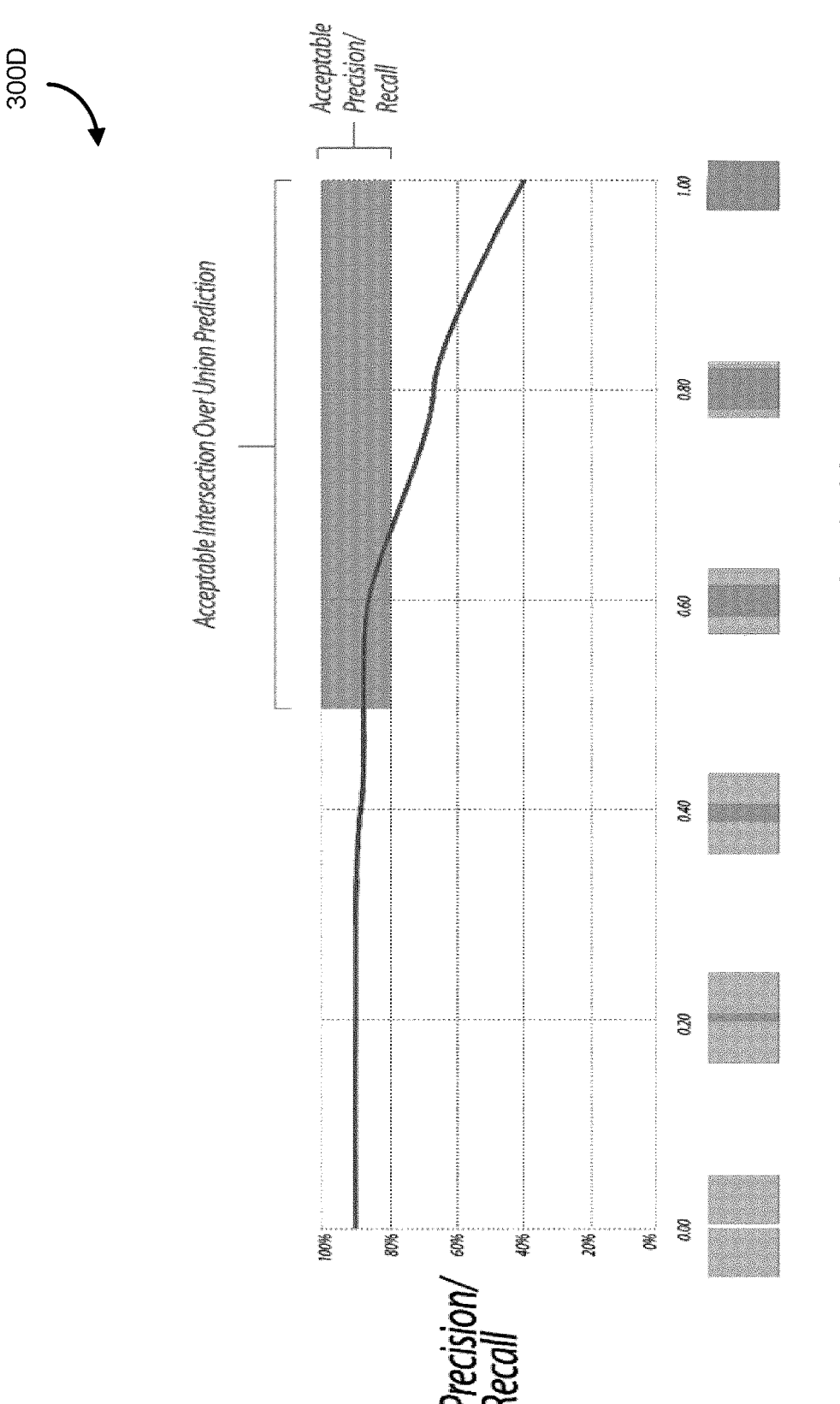
FIG. 3D is a chart showing an example trade-off between precision and recall and intersection of union prediction, according to some embodiments.
Figure 3E:
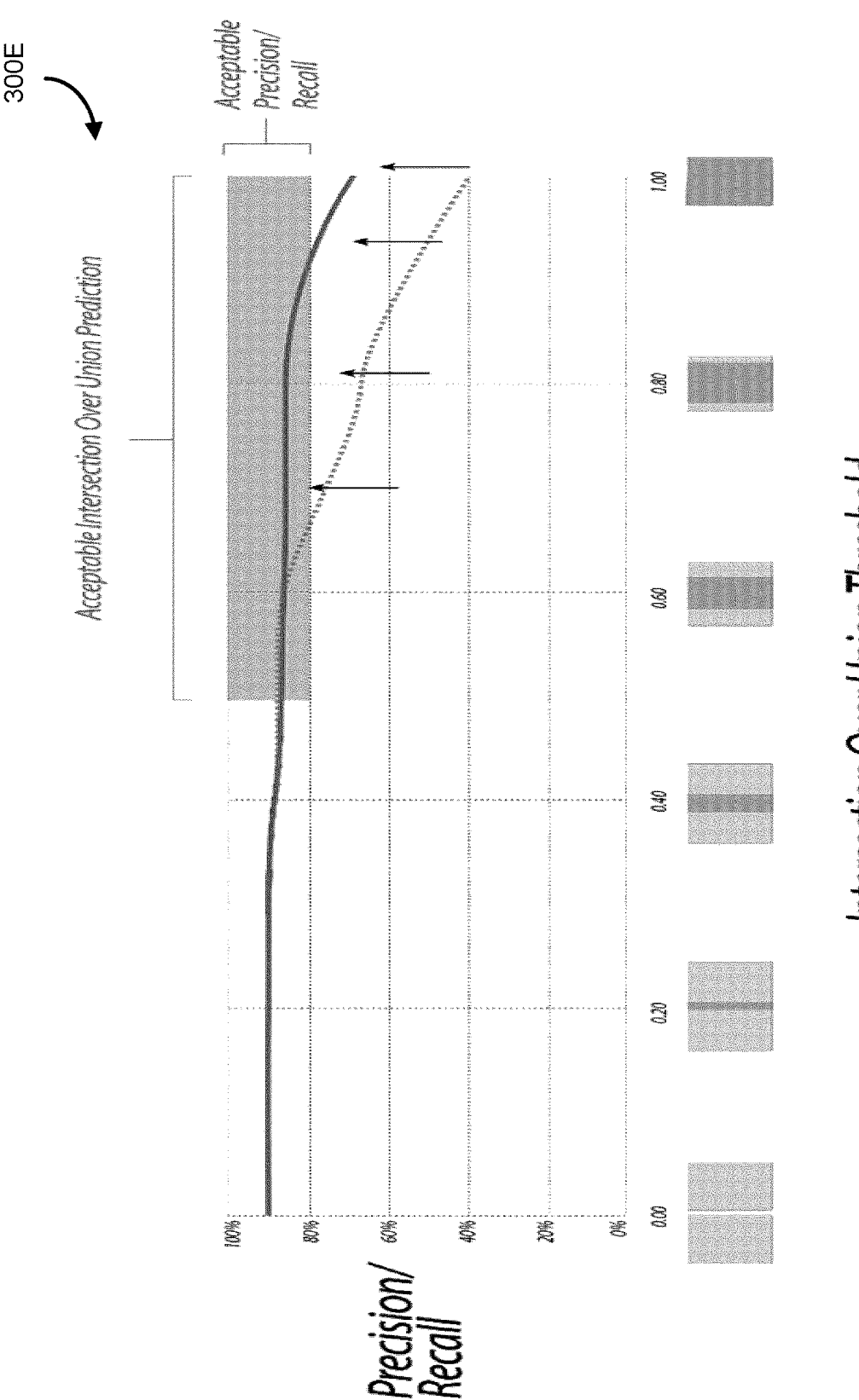
FIG. 3E is a chart showing an improved trade-off between precision and recall and intersection of union prediction, according to some embodiments.

FIG. 3D is a chart 300D showing an example trade-off between precision and recall and intersection of union prediction, according to some embodiments. FIG. 3E is a chart 300E showing an improved trade-off between precision and recall and intersection of union prediction, according to some embodiments. In these examples, a desirable area where there is a balance between an acceptable intersection over union prediction as well as a acceptable precision relative to recall is established.

Accordingly, in some embodiments, the system is adapted to tune itself over a period of time to maintain an acceptable balance (e.g., to improve the curve as shown by the arrows in FIG. 3E).

Figure 4:
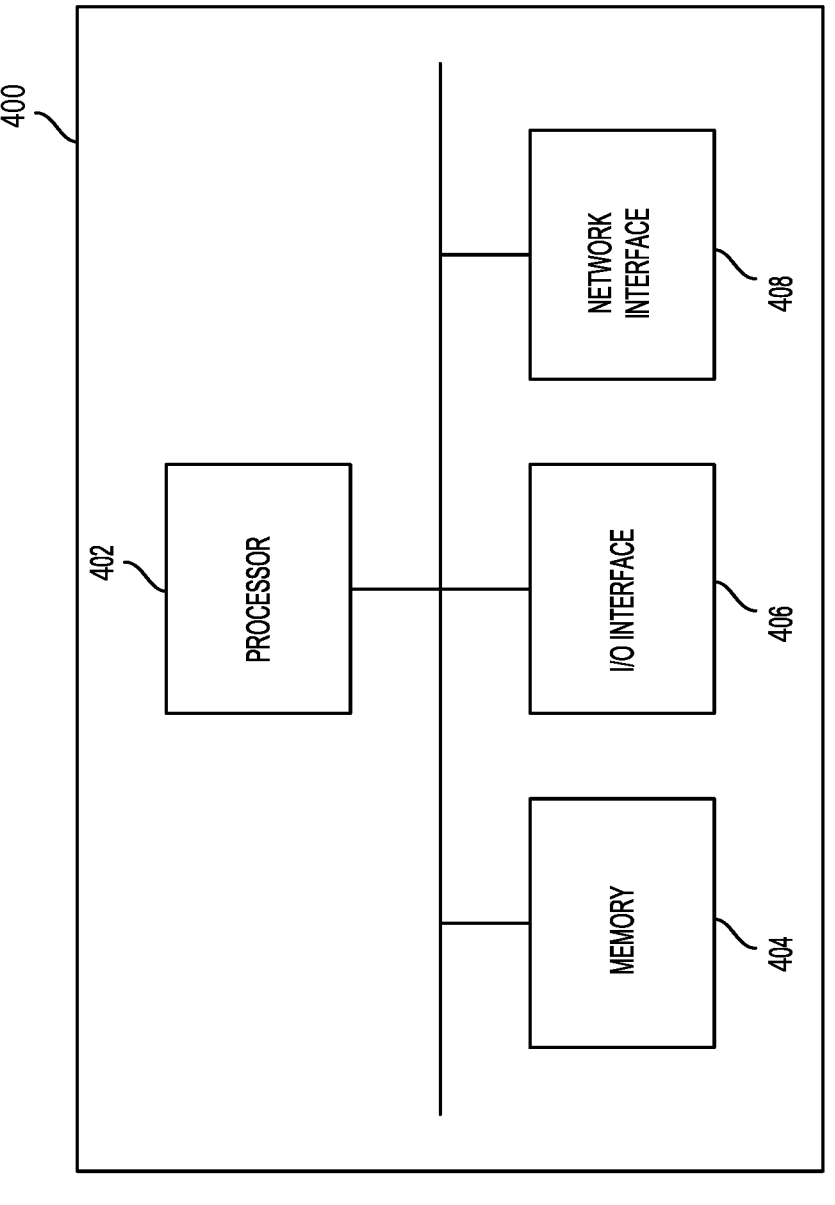
FIG. 4 is an example computer server for implementing one or more aspects of the embodiments described herein.

FIG. 4 is a schematic diagram of a computing device 400 such as a server adapted for automated de-identification. As depicted, the computing device includes at least one processor 402, memory 404, at least one I/O interface 406, and at least one network interface 408.

Processor 402 may be an Intel or AMD x86 or x64, PowerPC, ARM processor, or the like. Memory 404 may include a suitable combination of computer memory that is located either internally or externally such as, for example, random-access memory (RAM), read-only memory (ROM), compact disc read-only memory (CDROM).

Each I/O interface 406 enables computing device 400 to interconnect with one or more input devices, such as a keyboard, mouse, camera, touch screen and a microphone, or with one or more output devices such as a display screen and a speaker.

Each network interface 408 enables computing device 400 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including combinations of these.

Computing device 400 can be operable to register and authenticate users (using a login, unique identifier, and password for example) prior to providing access to applications, a local network, network resources, other networks and network security devices. Computing devices 400 may serve one user or multiple users.

Figure 5:
FIG. 5 is an example special purpose machine residing within a data center, according to some embodiments.
Figure 5:
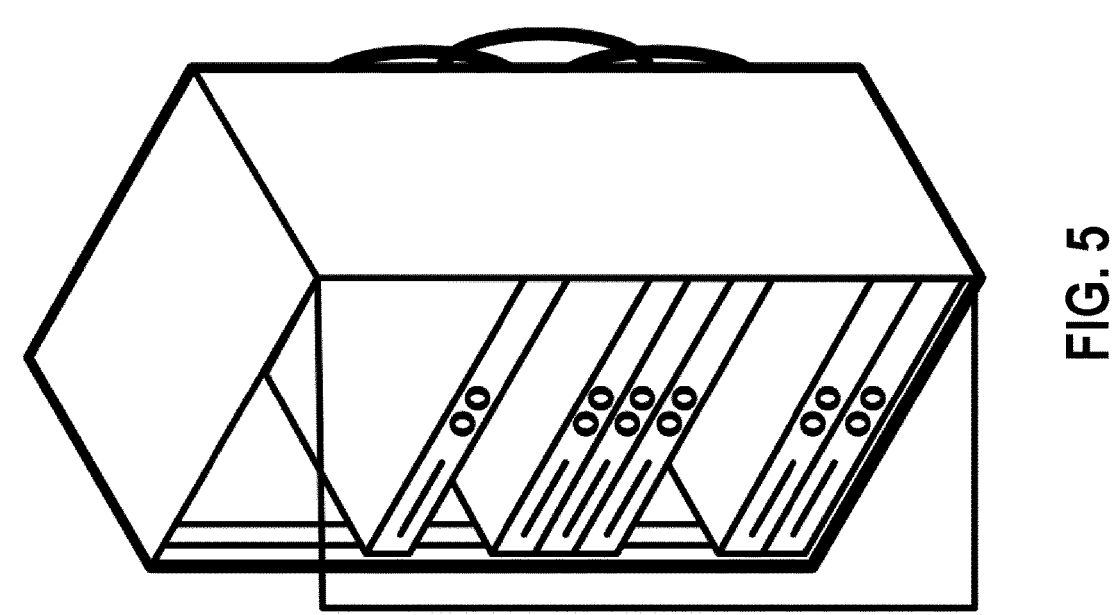

FIG. 5 is an example special purpose machine residing within a data center, according to some embodiments. In FIG. 5, device 500 may be implemented in the form of a rack mounted appliance that can reside in a data center and may be coupled to other computing devices to receive input data sets from a message bus, and to generate de-identified outputs on the message bus for communicating to downstream systems.

Figure 7A:
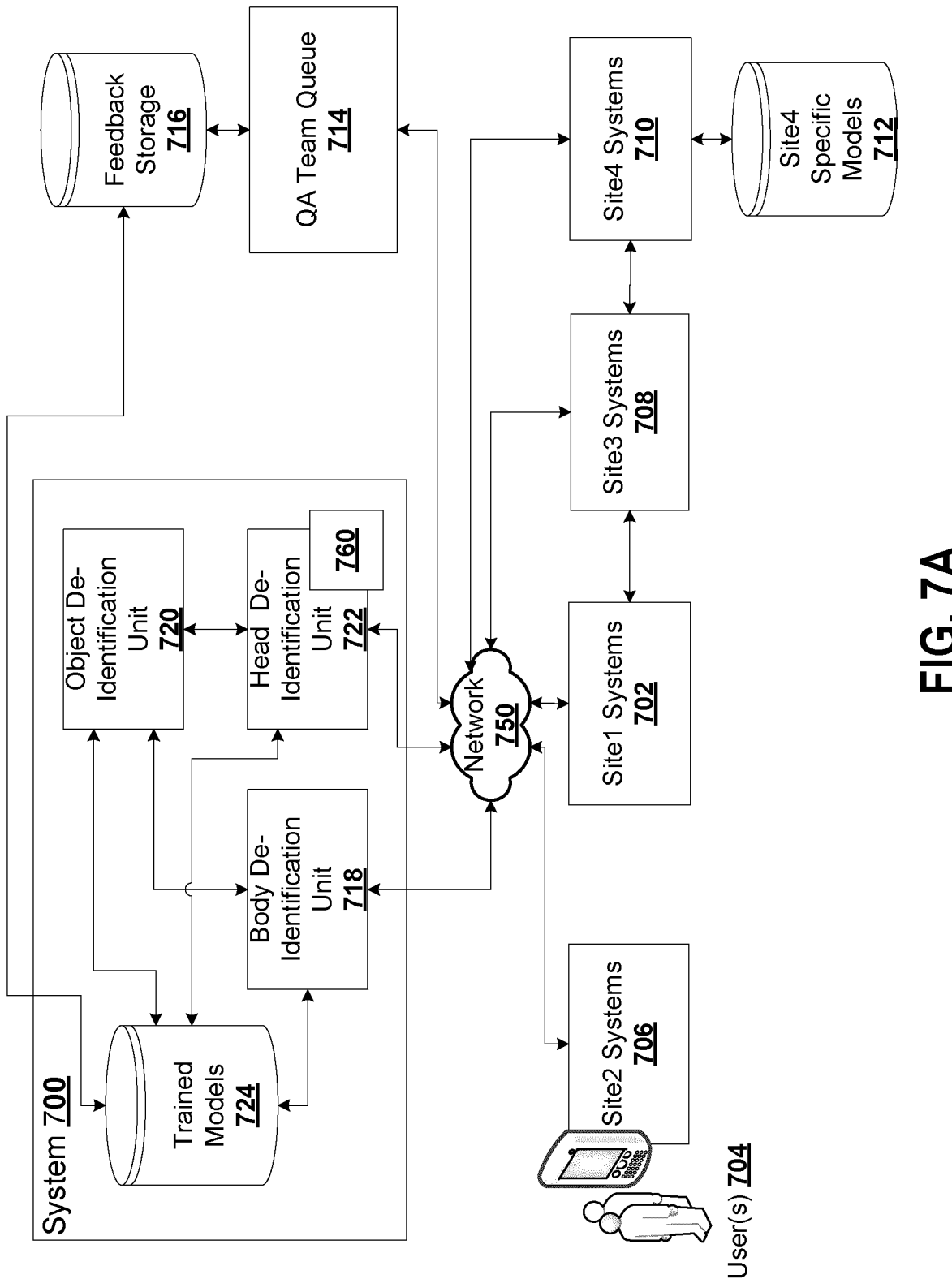
FIG. 7A is a block schematic showing various aspects of a system for de-identification, according to some embodiments.

FIG. 7A is a block schematic showing various aspects of a system for de-identification, according to some embodiments.

In FIG. 7A, an example system 700 is shown, which is a machine learning appliance configured for generating predictive data set outputs that can be utilized to transform audio or video data captured at a hospital operating room, or other types of facilities. In FIG. 7A, the system is provided as a computing appliance that connects to recording systems present at Hospital Sites, shown in example as 702, 706, 708, and 710, respectively. Each of these Hospital Sites can have different jurisdictional or local policies in place in respect of obfuscation requirements, and these may vary, for example, based on regulatory regimes in respect of identifiable information, hospital or hospital network specific policies, among others. In some embodiments, these obfuscation requirements are captured in the form of compliance instruction set data objects that are provided by each of the site systems, 702, 706, 708, and 710. The compliance instruction set data objects may also provide instruction sets as to how any output data or information will need to be formatted, and whether there are any retention requirements and/or automatic erasure requirements.

The system 700 can be provided on premises or off premises (e.g., provided through a cloud or through a secure network, such as within all of the associated hospitals for a particular hospital network), and can be coupled via a local area network or a wide area network through network 750. Where wide area networks are used or the internet is used, encryption may be applied to any incoming data streams before sending to be decrypted by system 700. The system 700 receives the data feeds from the systems 702, 706, 708, and 710, and the feeds can be provided in the form of real-time or archived audio or video files, such as files provided in .WAV formats, .MP3 formats, .AVI, .MP4, .WMV, formats, among others. In some embodiments, the input data objects further include metadata such as timestamps, properties, site identifiers, among others.

When the input data objects are received, they may include identifiable information. This identifiable information can include, for example, identifiable images of practitioners, such as surgeons and nurses, including their faces, identification badges, tattoos, voices, among others. The identifiable information can also include information regarding patients (e.g., patient faces, tattoos) captured in the input data objects, and from the operating theater (e.g., room numbers). There may also be sensitive information to be redacted. For example, a patient may have the patient's clothes removed, showing the patient's genital region or other sensitive regions due to the nature of the surgical procedure.

The input data objects are captured by, for example, recorders coupled to an "operating room" black box. The recorders can include cameras, microphones, instrument recordings, "smart" tools, wearables, among others. The operating room black box may be a central controller or coordination data processing engine that is configured to provide records of surgical procedures, or in further embodiments, conduct machine learning processing to generate insights or predictions, for example, by automatically ranking, rating, annotating, or otherwise generating metadata in accordance with the captured data. The operating room black box may be used in real-time, for example, in an attempt to automatically identify emergency situations, or asynchronously, such as to couple with adverse events or positive outcomes for analysis into reasons why a particular surgical procedure was successful or unsuccessful.

For example, a specific orthopedic surgeon may have a high post-operative success rate and the black box recordings can be used to identify whether there are particular useful leading practices to be extracted. Conversely, adverse outcomes can also be reviewed, for example, in line with predictive errors from a machine learning engine captured in the form of annotations for quick traversal of the recorded media to the areas of interest (e.g., an estimated bleeding or thermal injury event).

The nature of operating theatre recordings is sensitive, and as described herein, the system 700 can be utilized to conduct a "first pass" (or subsequent pass) de-identification such that the input data objects or streams can be transformed into a de-identified output that is a redacted or modified version of the input data objects. In another embodiment, the system 700 generates an intermediate output that is a set of instruction codes for generating the ultimate de-identified output.

The set of instruction codes can include instructions for an encoder to modify specific pixels or pixel regions or audio or audio regions of the recordings. For example, for each frame of a video or audio, an array of values can be provided for each pixel or each audio feature with a predictive output from the system 700 that indicates whether the pixel or each audio feature requires de-identification (e.g., 0.56, 0.9, 0.95, 0.1, 0.2). Where the pixel or audio feature has a value greater than a threshold (e.g., 0.5), the pixel or audio feature is flagged for transformation or obfuscation.

A flexible approach is described herein where a set of machine learning models can be used and trained for different tasks, and deployed flexibility without a priori knowledge of a particular site, types of objects, or people to be de-identified. The system 700 can be trained with supervised training sets from a variety of different settings, which do not necessarily need to even be hospital rooms or operating theatres.

A body de-identification unit 718 can be provided as a code module or processing engine that maintains a trained model that is configured for body segmentation and/or obfuscation. The body de-identification unit 718, in some embodiments, is trained using supervised learning to identify pixels associated with body parts or bodies of human beings (e.g., wearing clothing or no clothing). The supervised training includes tuning weights of the model through optimizing a loss function adapted for rewarding the system for correcting estimating that a particular pixel corresponds to a body part of a person, and/or penalizing the system for incorrectly estimating that a particular pixel corresponds to a body part if it does not actually have a body part, or missing a pixel associated with the body part. In the supervised training, the body de-identification unit 718 can be provided validated data sets where there is a known ground truth for comparison.

The body de-identification unit 718, for a particular frame, can then generate a pixel-by-pixel contour identified of border pixels associated with a particular human or body part, for example, as shown in FIG. 2B, at 204. All of the unobstructed human body part associated pixels corresponding to the body contour, for example, can be associated with a human.

In a variant embodiment, the body de-identification unit 718, upon identifying the body part associated with the human, generates a skeleton representation or DensePose (e.g., probability clouds) representation of the human body part and appends the data to a metadata track associated with a particular point in time and the corresponding video frame. This skeleton or DensePose metadata track output, for example, can include coordinates or relative positionings of various identified body anchor points, such as a pelvis, the beginning and end of legs/arms, abdomens, etc., and can be used for downstream analysis, for example, for identifying pelvic, genital or sensitive regions of patients or other individuals shown in the input data feeds. The body contour, DensePose, and skeleton outputs can also be used for identifying areas to be obfuscated.

Following identification of the pixel-by-pixel body contour, the input results indicative of where the body is can be passed alongside the input data stream or frames thereof to the head de-identification unit 722, which can be a separately trained model that is specifically configured or adapted for head detection. A number of different models can be used, such as R-FCN, and the head de-identification unit 722 may be trained to maintain a trained model tuned based on a specific supervised training that is directed to head object detection. The head de-identification unit 722 is configured to identify bounding boxes associated with heads, and to re-size, re-position, and re-shape the bounding boxes, for example, as the heads transition and move along with the bodies throughout temporally proximate frames. The bounding boxes associated with the heads can be used, for example, to generate a predictive output on a pixel-by-pixel basis (e.g., the areas covered by the bounding boxes or individual pixels).

An example output can be, for frame at t=0.5 s, a head is detected from x1, y1, to x2, y2, and all of the pixels within this box are flagged based on a confidence score obtained from the model of the head de-identification unit 722. In another embodiment, an example output can be, for the frame at t=0.5 s, a three dimensional array associating each pixel (x, y) with a value (pHead), such that every pixel in the video now has a tuple (x, y, pHead). In some embodiments, an additional momentum tracking engine 760 is provided that can be used for momentum interpolation or extrapolation of head data objects (or body contour objects) such that anchor points of the various bounding box representations of heads or bodies can be tracked over a temporally proximate set of frames (in some real-time embodiments, only backwards, in other non-real-time embodiments, forwards and backwards). If the head data object or body is determined to be moving through movements of the bounding box, the speed or movement of the head data object or body can be estimated through dividing the displacement over the timeframe in which the frames showing the movement cover. The speed or movement of the head data object can then be used to apply a transformation factor (e.g., size of bounding box increased in all directions by 5-50%) to dynamically resize the bounding box larger during times of movement, proportional to the detected speed of movement (e.g., 5% at a slow movement, and 50% at a very fast movement).

Dynamically re-sizing the bounding box in the way allows for the system to obtain further improvements in respect of avoiding false negatives, however, at the cost of increased false positives. This provides an additional technical mechanism to avoid deficiencies of the head object detection or the body detection model, especially where when using a model that is trained across multiple temporal frames at once for head or body object detection and relies on stability across frames for increased accuracy. In some embodiments, the enlarged area from the momentum interpolation or extrapolation is assigned a lower contribution score than the main bounding box or contour region, such that when the array is ultimately used for generating the de-identified output, different effects may be applied based on different thresholding (e.g., cartoonization vs. a full replacement of pixels vs. a blurring effect).

An object de-identification unit 720 may be a coding module or processing engine that is configured for identifying identifiable objects, such as decals, operating room numbers, identification badges, hospital names, among others, from the input data feed. Similar to the units 718 and 722, the object de-identification unit 720 maintains a separately trained model that can be used to generate predictive outputs, for example, on a pixel-by-pixel or a pixel region, or audio feature basis.

The trained models can be stored in data storage 724, and in some embodiments, the models can be common across all sites and deployed accordingly. In some embodiments, an additional set of site specific models 712 is maintained, and the additional site specific models 712 can be used for additional training epochs with data specific to a particular site, such as site 710, to improve accuracy of the models for that specific site. In Applicants' testing, this was found to be particularly beneficial and yielded superior results, potentially due to an improved ability for the models to focus on particular types of faces expected to be present at a particular site, or specific types of clothing worn at that site, or decals and other identifiable objects present. In some embodiments, the trained models themselves are configured with a level of tune-ability in their architectures that bias them towards a particular type of output, for example, being provided with two separate loss functions, a first loss function being optimized for reducing false negatives, and a second loss function being optimized for reducing false positives, and each of the predictive outputs is a weighted combination of these two outputs such that the system is tunable to balance between optimization for reducing false negatives or reducing false positives. For example, a user 704 at a user interface may be able to control, using an input device, a slider, or a knob, or input a value indicative of the relative weighting such that the weighting can be tuned or otherwise shifted. In respect of the specific context of de-identification, there is a bias towards preferring the reduction of false negatives, although there is a balance to be had with also avoiding the presence of so many false positives that the resulting output is not useful as an operating room black box recording.

The system 700, in this example, through the various units 718, 720, and 722, generates a set of predictive outputs that, for example, can represent the model predictive outputs associated with the confidence from each of the units that a particular pixel, pixel region, bounded box region, or audio feature represents identifiable information. Each of these outputs, for example, can be coupled as metadata in the form of a two or three dimensional array associated with each frame or timestamp step. The metadata can be provided in the form of tuples, such that, in a pixel example, at time=0.5 s, pixel (x,y), can have an associated tuple, (pBody, pHead, pObject), such as (0.8, 0.1, 0.1) for a body pixel in the body contour that is not the head, among others. Similarly, a tuple such as (0.1, 0.9, 0.1) can show the presence of a head (or simply fall within a head bounding box).

The system 700 can be configured to apply different approaches for tuning the output and de-identification transformations based on different weighted combinations of each of the contributions from each tuple for generation of a de-identification mask array. For example, each tuple could be compressed through applying a weighting factor, such as A×pBody, B×pHead, and C×pObject can be applied, where A, B, and C, add up to one, and the system can be tuned to apply different weightings to different types of predicted identifications based on a particular policy. In respect of de-identification for operating theatres, the system can, in an embodiment, be configured to apply strict and heavy weightings to removal of heads or genitals, etc., and weight any pixel having those characteristics estimated more heavily.

The mask array can be stored as a data object and provided to an encoder for re-encoding the input data stream to generate an output data object. The encoder, in some embodiments, is configured to transform or obfuscate specific audio or video frame pixel objects based on whether the mask data object value corresponding to the particular specific audio or video frame pixel object has a value greater than a threshold value, such as 0.3. In some embodiments, the encoder applies different levels of different types of obfuscation depending on different threshold levels. For example, if the value is between 0.3 and 0.5, a cartoonization effect is applied, between 0.5 and 0.8, a blurring effect is applied, and between and 1.0, the pixel is simply replaced with black. For audio, similarly, for 0.3 to 0.5, the pitch is changed, for 0.5 to 0.8, a cadence is changed along with a pitch, and from 0.8 to 1.0, the audio is simply removed.

Following encoding, the output data object is transformed and can be provided to a QA team queue 714 for final review and analysis. In some embodiments, a confidence score array is also provided to the QA team queue 714 as an additional metadata track so that the QA team queue 714 can observe where the system 700 had low confidence in the outputs. In some embodiments, the re-annotations from the QA team queue 714 are stored in feedback storage 716 as new supervised learning sets for re-training of the trained models 724.

FIG. 7B is a method diagram 700B showing an example method for de-identification, according to some embodiments.

In method 700B, the models are trained at 772, and optionally, site-specific training epochs can be applied to further tune the models for use and deployment at a particular site. The original black box data recordings are obtained at 774, and these are processed as described above at 776 to generate the encoding instructions for generating the ultimate de-identified data recordings at 778. The original data streams can be processed by other machine learning mechanisms of the black box controller, such as predictive estimation of potential events, such as thermal injuries, bleeding events, poor sanitization, high surgical skill, low surgical skill, among others, to generate various types of metadata outputs, which can be stored alongside the de-identified data recordings at 780 to provide an archive-able record of the surgical event for future analysis absent specific identifying information. Depending on the specific retention policy, the original, identifiable recording can then be deleted at 782.

Experimental Validation

Applicants have implemented various test iterations and implemented an example configuration model in accordance with FIGS. 13-16, at 1300, 1400, 1500, and 1600.

In the test configuration of the approach, the system was utilized across multiple test cases, in different sites. In testing, the Applicants were able to obtain improvements in relation to decreases in computational requirements (e.g., 8× real-time to ~1× real-time), and attempted approaches using additional human-in-the-loop quality assurance processes. An additional annotation and fine-tuning approach were also implemented.

Additional test results are described below in respect of a real-world deployment in accordance with an example embodiment that provided good performance across multiple test cases.

In a first test case described herein, a data set is provided where 5-second video clips were obtained from three different sites. All of the video clips are real surgeries with visible patients and surgical team members.

Each clip is annotated with two detection type 'Head' and 'Patient'.

The model is trained on videos from HospitalSite2 and HospitalSite3, which can be considered as a test set. The model is not trained on videos from HospitalSite1, which can be considered as the transfer learning test set.

Table 3 below shows the test setup.

| site | #camera | #case | #clip |
|---|---|---|---|
| Hospital Site 1 | 2 | 9 | 18 |
| Hospital Site 2 | 3 | 9 | 27 |
| Hospital Site 3 | 2 | 9 | 18 |

For removing identifying features of people in the operating room, head blurring was provided as a main component in the de-identification process. In particular, head blurring, in the experimental approach, was built with Operating Room Head Detection, with a R-FCN model being utilized, pretrained on MS-COCO, fine-tuned on Applicant's Head Dataset (cases from HospitalSite4, HospitalSite1, HospitalSite3, HospitalSite5), and also fine-tuned on Applicant's Head+Patient Dataset (cases from HospitalSite2, HospitalSite3).

Evaluation on head blurring uses metrics in a combined manner of detection and mask. For one frame, the system is configured to optimize about what proportion (e.g., how much percentage) of a region of interest is covered by true positives.

Figure 8:
FIG. 8 is an illustration showing an example region of interest mapping, according to some embodiments.
Figure 8:
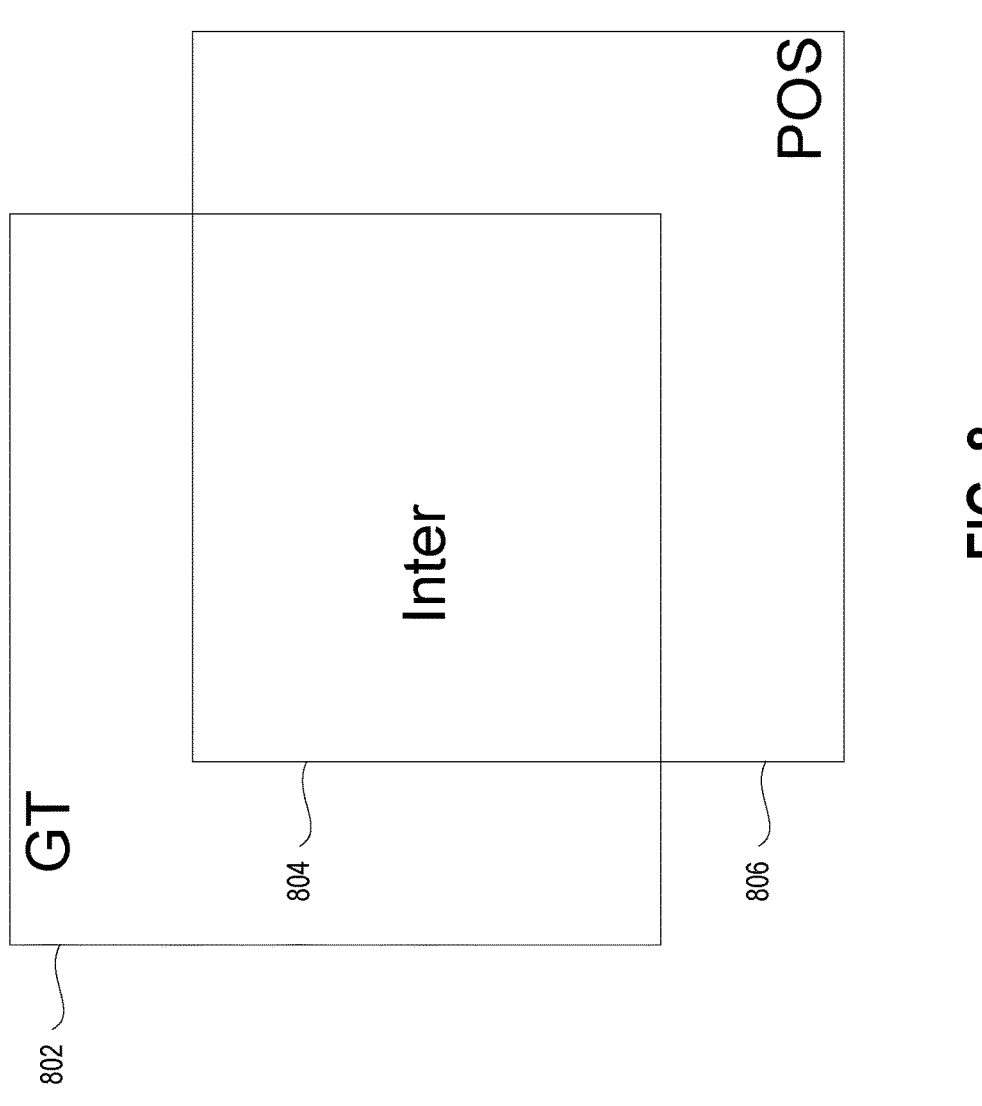

FIG. 8 is an example rendering 800 of a percentage of ROI being covered by a true positive. In this example, a number of metrics are shown. Recall is a characteristic that indicates how many ground truth are detected. For one frame, if the pixel percentage of (true positive (inter 804)/ ground truth (inter 804+GT 802)) is over the threshold, recall on this frame is set to the percentage; otherwise, it is set to 0.

Precision a characteristic that indicates how many detection are real heads. For one frame, if the pixel percentage of (true positive (inter 804)/positive (inter 804+pos 806)) is over the threshold, precision on this frame is set to the percentage; otherwise, it is set to 0. Lower thresholds can have higher recall/precision. Overall recall/precision can be averaged among all frames.

Considering the problem definition and method of detection, Applicants made a a number of changes to the approach for determining of recall and precision as a function of the meaning of coverage:

recall: true positive coverage rate: Applicants determine pixel percentage for each frame such as 0.8 (not 1 if over threshold as traditional recall), and then obtain an average on the various frames;

precision: positive predictive coverage rate: Applicants determine pixel percentage for each frame such as 0.8 (not 1 if over threshold as traditional recall), and then obtain an average on the various frames.

Accordingly, Applicants are then able to use the true percentage on each frame, lower than commonly-used 1.0, and this could be a reason why an output result is lower than reported on similar papers. Specifically, recall=0.8 does not mean 20% of objects are missed.

Figure 9A:
FIG. 9A illustrates experimental results of an example system used to de-identify features from a video obtained at a first hospital site.
Figure 9B:
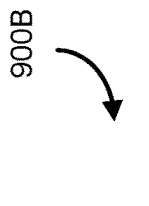
FIG. 9B illustrates experimental results of an example system used to de-identify features in from a video obtained at a second hospital site.

Intersection threshold shows how strictly when comparing prediction and ground truth. The values vary from 0 to 1. FIG. 9A illustrates experimental results of an example system used to de-identify features from a video obtained at a first hospital site HospitalSite1. FIG. 9B illustrates experimental results of an example system used to de-identify features in from a video obtained at a second hospital site HospitalSite2. These experimental results are obtained on setting of sampling_rate=5, batch_size=24.

As can be seen from FIG. 9A and FIG. 9B, for commonly used thresholds 0.5 and and the disclosed model behaves basically similar on these for HospitalSite2 and HospitalSite3, meaning predicted bounding boxes are precise. When threshold is set at 1.0, some of recalls/precisions may be found not to be approaching 0. This is because for frames having no head or patient, the frames may be marked as 1 for both recall and precision (meaning this frame has been de-identified properly). The result from HospitalSite1 is worse than HospitalSite2/HospitalSite3, meaning that site-specific fine-tuning may be necessary. For example, fine-tuning with data from the specific site can be utilized to use a few weeks worth of data (e.g., two weeks), and a limited number of of additional training epochs on the new data, with or without penalties applied to the loss function to slow or speed the training process.

Figure 10A:
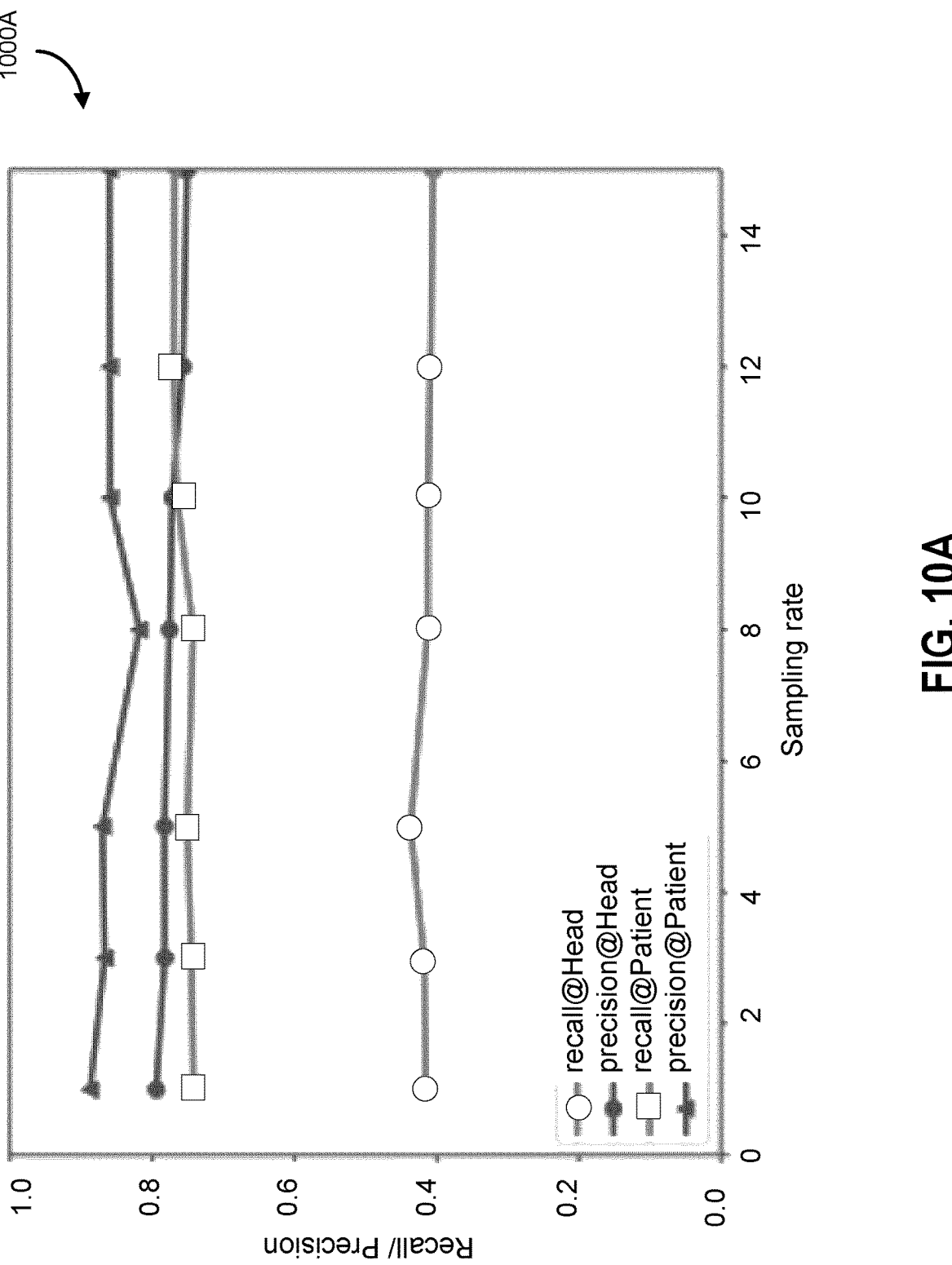
FIG. 10A illustrates experimental results of an example system used to de-identify features from the video obtained at a first hospital site using different sampling rates.
Figure 10B:
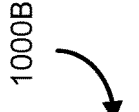
FIG. 10B illustrates experimental results of an example system used to de-identify features in from a video obtained at a second hospital site using different sampling rates.

In some experiments, only key frames are sampled and detected on the input videos, with some frames skipped between the frames. This will not affect when people stay still (most cases) but the result may be inferior when people move fast in the operating room in a given time frame. FIG. 10A illustrates experimental results of an example system used to de-identify features from the video obtained at a first hospital site HospitalSite1 using different sampling rates. FIG. 10B illustrates experimental results of an example system used to de-identify features in from a video obtained at a second hospital site HospitalSite2 using different sampling rates. The value for K may vary from 1 to 15. This is evaluated on setting of P/R threshold=0.5, batch_size=24.

As can be seen from FIG. 10A and FIG. 10B, missed detection can be fixed by adding smoothing at beginning/end of each trajectory. Sampling less and missing a few may not impact the performance significantly and can be fixed by momentum-based smoothing.

Smoothing is added at beginning/end with K key frames. When the sampling rate is larger, the number of smoothed frames is greater, fixing is better, recall is higher, and precision is lower. Momentum is determined by average speed at beginning/end. When the sampling rate is larger, the momentum is more stable, and the trajectory is more smooth. In addition, fixing can fail when momentum cannot represent the missing movement, especially when acceleration is higher, such as when a direction of one or more objects is changed quickly, or when one or more objects are moving or accelerating at a rate that is above a threshold.

Figure 11:
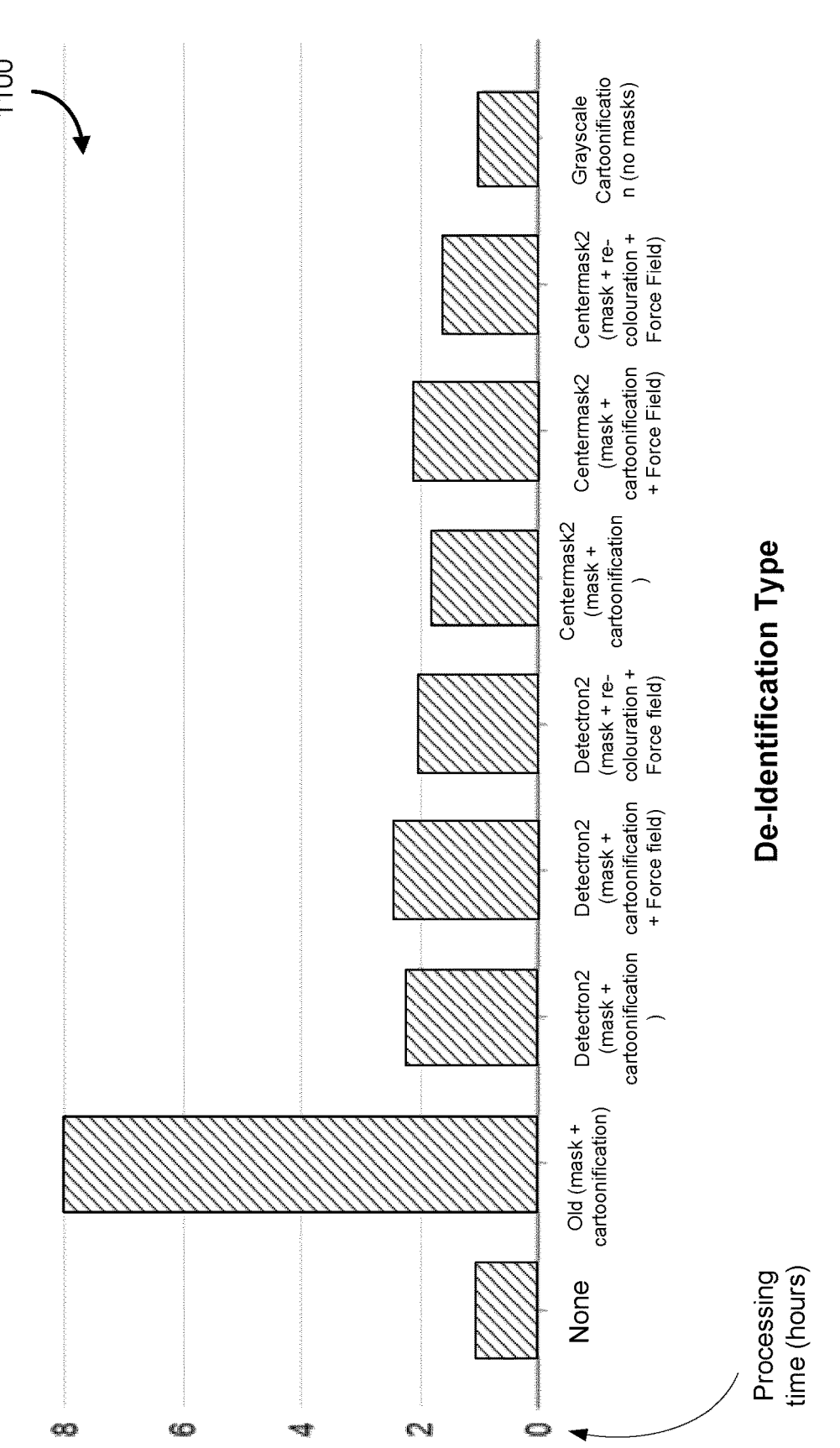
FIG. 11 illustrates example processing time of various de-identification types in hours in a first chart.

FIG. 11 illustrates example processing time of various de-identification types in hours in a first chart, for both head and body. As can be seen, prior method with mask and cartoonification takes a lot more time than Detectron2 and Centermask2 methods.

Figure 12:
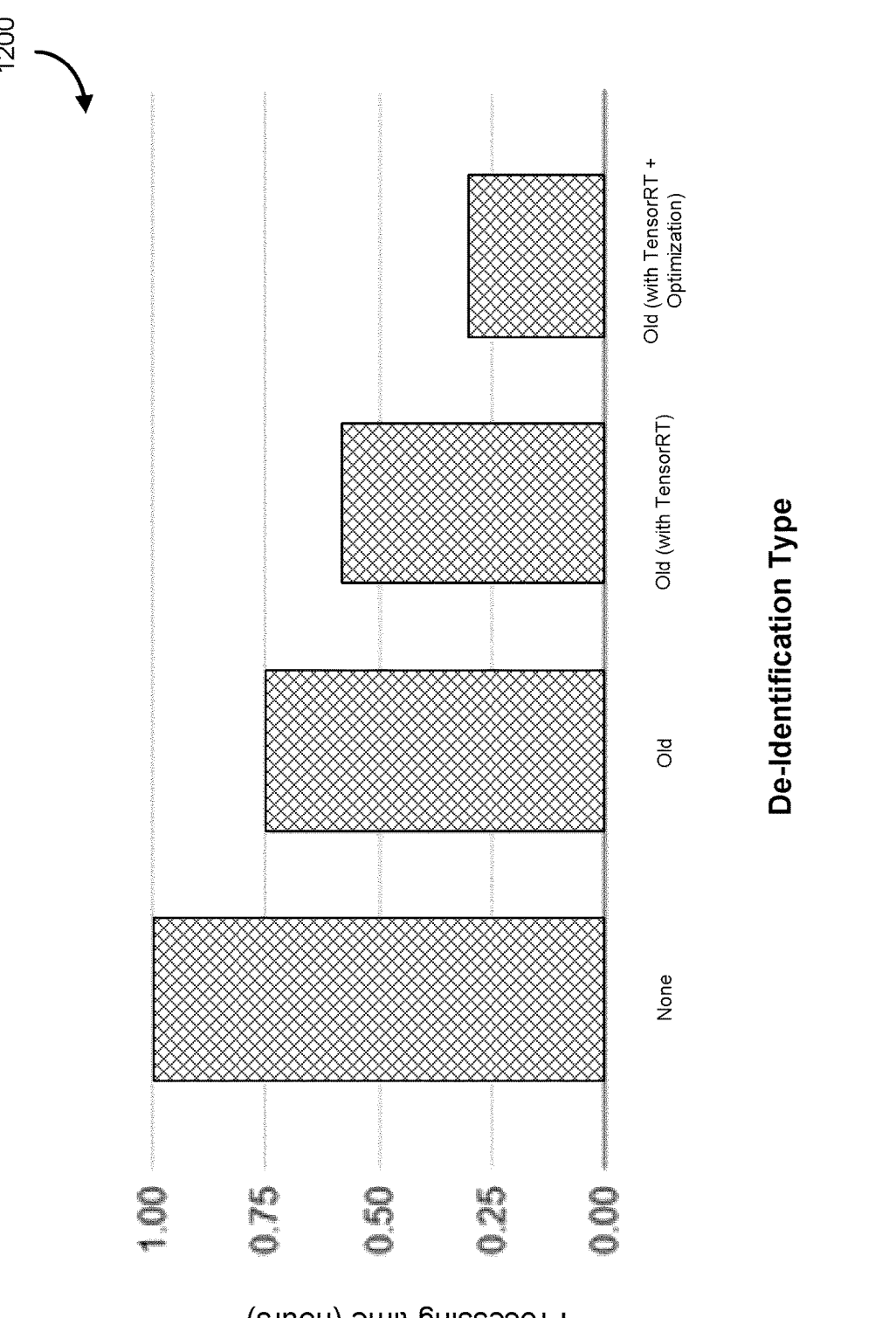
FIG. 12 illustrates example processing time of various de-identification types in hours in a second chart.
Figure 14:
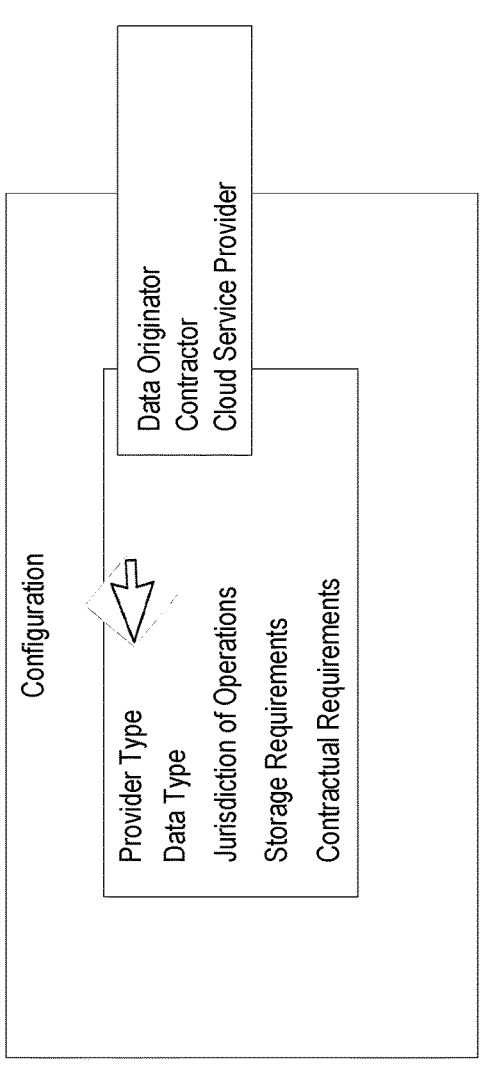
Figure 15:
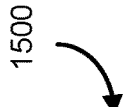
Figure 15:
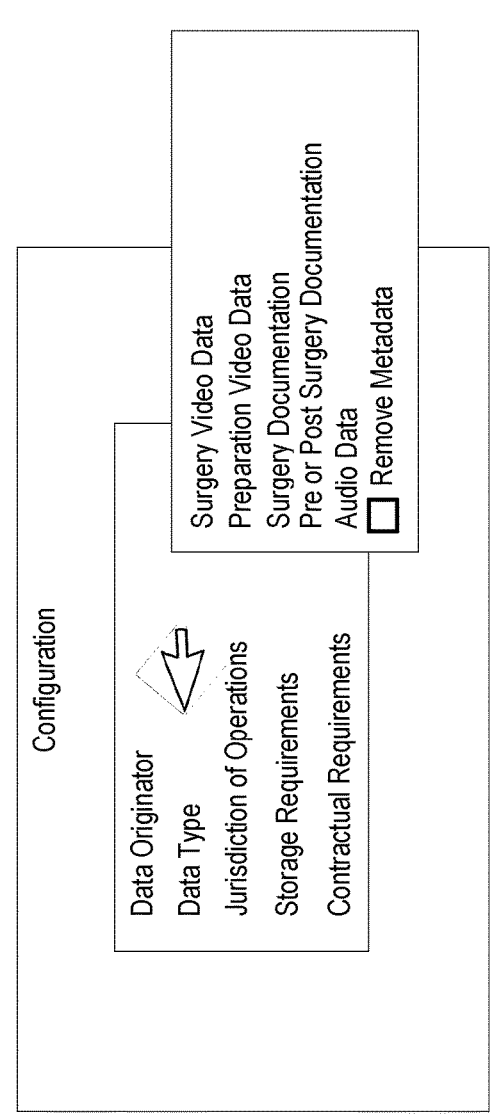
Figure 16:
Figure 16:
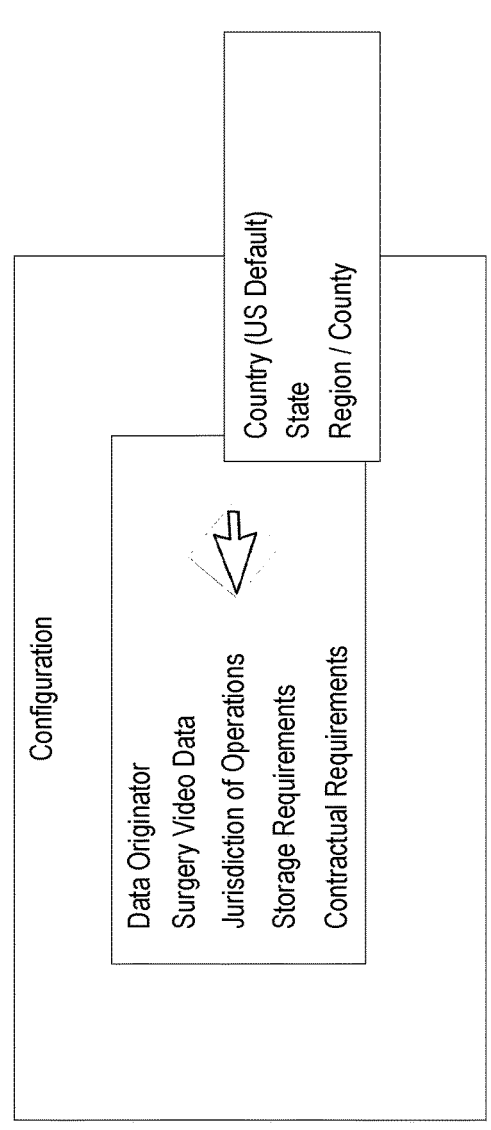

FIG. 12 illustrates example processing time of various de-identification types in hours in a second chart. As can be seen, tensorRT performs better (less time) with optimisation than without optimisation.

For false negative rate (FNR), the experimental results obtained from HospitalSite1 video has a FNR of 0.24889712, the experimental results obtained from HospitalSite2 video has a FNR of 0.14089696, and the experimental results obtained from HospitalSite3 video has a FNR of 0.21719834.

For false discovery rate (FDR), the experimental results obtained from HospitalSite1 video has a FDR of 0.130006, the experimental results obtained from HospitalSite2 video has a FDR of 0.20503037, and the experimental results obtained from HospitalSite3 video has a FDR of 0.09361056.

Test Case Results (HospitalSite6)

The tables below show example test case results in respect of various types of surgical videos. In the test cases below, the model performed well in most cases, but in situations, there still can be post processing conducted by a quality assurance final step to handle unseen tools (e.g., those causing reflection, plastic wrap, and remaining names on ultra-sound feed, etc.).

TABLE 4

| | | | | Model |
|---|---|---|---|---|
| | | | | Robotic-assisted laparoscopic surgery |
| Case ID | Start Time | End Time | Clip Description | Behavior |
| 0c537f87__1005105__20200803T032057__008 | 00:09:30 | 00:10:30 | Blue - noise - external | Perfect |
| 0c537f87__1005105__20200803T032057__010 | 00:03:30 | 00:06:30 | External - internal | Transition not perfect, false positives on tool reflections |
| 0c537f87__1005105__20200803T032057__010 | 00:22:30 | 00:24:30 | Single stream - double stream | Perfect, patient name need to be blurred |
| 0c537f87__1005105__20200803T152737__000 | 00:00:30 | 00:03:00 | Internal (plastic) | False positives |
| 7ecc81cb__1006105__20200803T032101__007 | 00:54:00 | 00:56:00 | Blue - noise - color | Perfect |
| 7ecc81cb__1006105__20200803T032101__009 | 00:09:30 | 00:13:30 | Internal - transition - internal - external | Perfect |
| 090de799__1006105__20200803T153043__001 | 00:51:30 | 00:53:00 | External - internal (anchor) - internal | Perfect |

The below testing data is for practical testing of de-identification of room video in an example operating room, Operating Room 5. In the practical testing, a number of issues arose in respect of bright region when lights are turned on, situations where surgical machines causes much occlusion (or people are inside the robotic surgery operating theatre), and in this particular site, there were higher occlusion rates. Face shields also caused issues, and the patient body mask required touch up annotation by quality assurance personnel.

TABLE 5

| | | | | | Site Specific |
|---|---|---|---|---|---|
| | | | Clip | Model | Model's |
| | | | Operating Room 5: | | |
| Case ID | Start Time | End Time | Description | Behavior | Behavior |
| 0c537f87__1005001__20200803T032057__003 | 00:13:30 | 00:14:00 | UVC clean | Perfect | Perfect, some false positives during UVC |
| 0c537f87__1005001__20200803T032057__008 | 00:43:30 | 00:44:00 | High traffic | Some heads missing due to occlusion | Head drops a little around pole |
| 0c537f87__1005001__20200803T032057__010 | 00:00:00 | 00:00:30 | Light on | Minor head missing under light | Perfect |
| 0c537f87__1005001__20200803T032057__010 | 00:44:00 | 00:44:30 | Davinci on | Perfect | Perfect |
| 0c537f87__1005001__20200803T144532__001 | 00:05:30 | 00:06:00 | Low traffic | Minor head missing under light | Perfect |
| 0c537f87__1005001__20200803T144532__001 | 00:28:30 | 00:29:00 | After, cleaning | Minor head missing under light | Perfect |

TABLE 6

| Operating Room 6 | | | | | |
| --- | --- | --- | --- | --- | --- |
| Case ID | Start Time | End Time | Clip Description | Model Behavior | Site Specific Model's Behavior |
| 7ecc81cb__1006001__20200803T094844__002 | 00:22:30 | 00:23:00 | High traffic | Mask missed, patient/ surgical mis-classified | Perfect |
| 7ecc81cb__1006001__20200803T094844__002 | 00:41:30 | 00:42:00 | Light on | One mask missed under light, one head missed with face shield | Perfect |
| 7ecc81cb__1006001__20200803T094844__002 | 00:50:00 | 00:50:30 | Light off | Mask missed under occlusion | Perfect |
| 7ecc81cb__1006002__20200803T032101__008 | 00:48:00 | 00:48:30 | Patient prep | Perfect | Perfect |
| 7ecc81cb__1006002__20200803T032101__009 | 00:10:00 | 00:10:30 | Light diff | Mask missed under light | Perfect |
| 7ecc81cb__1006002__20200803T032101__009 | 00:48:30 | 00:49:00 | Davinci | Mask missed under occlusion | One mask flicker under occlusion |
| 7ecc81cb__1006003__20200803T094845__001 | 00:51:00 | 00:51:30 | Cleaning | Perfect | Perfect |
| 7ecc81cb__1006003__20200803T094845__002 | 00:34:00 | 00:34:30 | Low traffic | Perfect | Perfect |
| 7ecc81cb__1006004__20200803T032101__009 | 00:11:00 | 00:11:30 | Light on | Mask missed under light | Perfect |
| 7ecc81cb__1006004__20200803T032101__009 | 00:45:00 | 00:45:30 | Light off | Head and mask missed in operating machine | Perfect |
| 090de799__1006001__20200803T131841__001 | 00:00:00 | 00:00:30 | Davinci | One mask missed | Perfect |
| 090de799__1006001__20200803T131841__003 | 00:39:30 | 00:40:00 | Crowded | Head and mask missed | Perfect |
| 090de799__1006002__20200803T131841__003 | 00:27:45 | 00:28:15 | Occlusion | Perfect | Perfect |
| 090de799__1006003__20200803T131841__003 | 00:46:00 | 00:46:30 | Occlusion | Perfect | Perfect |
| 090de799__1006004__20200803T131841__003 | 00:19:00 | 00:19:30 | Crowded | Mask missed under occlusion | Perfect |
| 090de799__1006004__20200803T131841__004 | 00:43:00 | 00:43:30 | Occlusion | Head missed under occlusion | Perfect |

TABLE 7

| Operating Room 7 | | | | | |
| --- | --- | --- | --- | --- | --- |
| Case ID | Start Time | End Time | Clip Description | Model Behavior | Site Specific Model's Behavior |
| 630272a3__1007001__20200803T094846__002 | 00:26:30 | 00:27:00 | Occlusion | Perfect | Perfect |
| 630272a3__1007001__20200803T094846__002 | 00:50:00 | 00:50:30 | Occlusion, light on | One head missed | Perfect |
| 630272a3__1007001__20200803T094846__004 | 00:24:30 | 00:25:00 | Low traffic | One head missed under light | Perfect |
| 630272a3__1007001__20200803T094846__007 | 00:21:00 | 00:21:30 | Occlusion | One head missed under occlusion | Perfect |
| 630272a3__1007001__20200803T094846__007 | 00:32:00 | 00:32:30 | Crowded | One head missing on monitor reflection | One head missing on monitor reflection |
| 630272a3__1007002__20200803T032105__009 | 00:17:00 | 00:17:30 | Light on | Mask flicker | Perfect |
| 630272a3__1007002__20200803T032105__009 | 00:25:30 | 00:26:00 | Occlusion | Perfect | Perfect |
| 630272a3__1007002__20200803T032105__010 | 00:30:00 | 00:30:30 | Occlusion | Mask missed under occlusion | One mask flicker under occlusion |
| 630272a3__1007002__20200803T032105__010 | 00:55:00 | 00:55:30 | Low traffic | Mask flicker | Perfect |
| 630272a3__1007002__20200803T032105__016 | 00:31:00 | 00:31:30 | Light changes | Perfect | Perfect |
| 630272a3__1007002__20200803T032105__016 | 00:54:15 | 00:54:45 | Roll out | Perfect | Perfect |
| 630272a3__1007003__20200803T032105__012 | 00:31:00 | 00:31:30 | Clean | Perfect | Perfect |

TABLE 7-continued

| | | | | | Site Specific Model's |
|---|---|---|---|---|---|
| Case ID | Start Time | End Time | Clip Description | Model Behavior | Behavior |
| 630272a3__1007004__20200803T094839__002 | 00:25:00 | 00:25:30 | Prep | Perfect | Perfect |
| 630272a3__1007004__20200803T094839__002 | 00:56:30 | 00:57:00 | Davinvi set-up | One head missed under occlusion | One head missed under occlusion and movement |

TABLE 8

| | | | | | Site Specific Model |
|---|---|---|---|---|---|
| Case ID | Start Time | End Time | Clip Description | Model Behavior | Behavior |
| Operating Room 8: | | | | | |
| 4937176f__1008001__20200803T132255__001 | 00:00:00 | 00:00:30 | Low traffic | Mask flickers for people in operating machine | Perfect |
| 4937176f__1008001__20200803T132255__001 | 00:29:30 | 00:30:00 | Davinci | One mask missed under occlusion | Perfect |
| 4937176f__1008001__20200803T132255__005 | 00:14:30 | 00:15:00 | Light on | Mask missed under light | Perfect |
| 4937176f__1008001__20200803T132255__005 | 00:38:00 | 00:38:30 | High traffic | Patient mask flickers | Perfect |
| 4937176f__1008002__20200803T132255__000 | 00:14:00 | 00:14:30 | Occlusion | Mask misses for people in operating machine | Perfect |
| 4937176f__1008002__20200803T132255__000 | 00:42:00 | 00:42:30 | Occlusion | Head misses for people in operating machine | Perfect |
| 4937176f__1008003__20200803T132255__005 | 00:10:30 | 00:11:00 | Light on | Perfect | Perfect |
| 4937176f__1008004__20200803T132255__001 | 00:40:30 | 00:41:00 | Occlusion | Head misses under occlusion | Perfect |
| fddd54bf__1008001__20200803T032112__009 | 00:03:45 | 00:04:15 | Prep | Head misses under occlusion | Perfect |
| fddd54bf__1008001__20200803T032112__009 | 00:13:00 | 00:13:30 | Crowded | Perfect | Perfect |
| fddd54bf__1008001__20200803T032112__009 | 00:40:00 | 00:40:30 | Light on | Perfect | Perfect |
| Operating Room 30: | | | | | |
| 8a79331a__1030001__20200803T130901__001 | 00:05:30 | 00:06:00 | Davinci | Mask misses under occlusion | Perfect |
| 8a79331a__1030001__20200803T130901__001 | 00:32:00 | 00:32:30 | Post surgery | Perfect | Perfect |
| 8a79331a__1030001__20200803T130901__001 | 00:58:00 | 00:58:30 | Roll out | Head misses under occlusion | One head missing on monitor reflection |
| 8a79331a__1030001__20200803T130901__007 | 00:54:00 | 00:54:30 | Clean | Perfect | Perfect |
| 8a79331a__1030002__20200803T130901__001 | 00:10:00 | 00:10:30 | Occlusion | Head and mask miss under occlusion | Two head missing under occlusion |
| 8a79331a__1030002__20200803T130901__001 | 00:58:00 | 00:58:30 | Roll out | Perfect | One head missing under occlusion |
| 8a79331a__1030003__20200803T130901__001 | 00:10:00 | 00:10:30 | Light changing | Head and mask miss under light | Perfect |
| 8a79331a__1030003__20200803T130901__001 | 00:38:00 | 00:38:30 | Low traffic | Perfect | Perfect |
| 8a79331a__1030003__20200803T130901__003 | 00:04:00 | 00:04:30 | Crowded | Small head misses | Two mask drop under occlusion |

TABLE 8-continued

| Case ID | Start Time | End Time | Clip Description | Model Behavior | Site Specific Model Behavior |
|---|---|---|---|---|---|
| 8a79331a__1030003__20200803T130901__003 | 00:35:00 | 00:35:30 | Low traffic | Head and mask flicker under occlusion | One mask flicker under occlusion |
| 8a79331a__1030004__20200803T130901__003 | 00:36:00 | 00:36:30 | Occlusion | Head misses under occlusion | One head and body miss under occlusion |
| 8a79331a__1030004__20200803T130901__003 | 00:48:00 | 00:48:30 | Occlusion | Head misses under face shield | Perfect |
| 8a79331a__1030004__20200803T130901__008 | 00:04:00 | 00:04:30 | Clean | Perfect | Perfect |
| 8a79331a__1030004__20200803T130901__008 | 00:25:30 | 00:26:00 | Clean | Perfect | Perfect |
| 583ce647__1030001__20200803T032115__009 | 00:37:00 | 00:37:30 | Light changing | Head and mask miss under occlusion | One head miss |
| 583ce647__1030001__20200803T032115__009 | 00:42:30 | 00:43:00 | Davinci | Head misses under occlusion | One head misses under occlusion |
| 583ce647__1030004__20200803T032115__009 | 00:12:00 | 00:12:30 | Prep | Perfect | Perfect |

Data Requirements for Model Fine-Tuning

As video features differ from site to site and OR to OR, Applicants collected data from a site operating room to fine-tune the head detection model, preferring real operation videos as opposed to simulated operation videos (although simulations may also help). When capturing operating room data, the type of operating room may be relevant (e.g., trauma operating rooms as opposed with normal operating rooms).

For example, the following characteristics may impact the head detection model:

amount of head: one may observe several surgical beds in one trauma OR and much more people than normal OR (6-12) size of head: as the OR is larger, size of each head may be smaller appearance: people in trauma OR may wear normal clothes or uniforms, other than surgical cap/gown surgical mask: people in trauma OR may enter without a surgical mask motion: people may move fast for emergency All these concerns may cause false negatives on the existing head detection model, and there may be a need to sample enough data to cover these cases.

A data request was submitted for 1500 images for training (1000), validation (200) and testing (300). Images should be sampled with a minimum gap of 5 seconds to maximize the data variance. Applicants suggest sampling 90% of data during operation and 10% of data when idle. This will take approximately about 5-8 days to finish head bounding box annotation by one AI analyst, for example.

Simulation data may also be used, for example, before official deployment and/or training to determine model performance. If model performance is comparable, the issue of bringing sensitive data on-site will be mitigated.

Data requirements during operation:

Videos from all 4 cameras of the trauma bay

Videos from all 4 cameras of a surgical room (multiple rooms would be even better) Videos with a real person wearing a patient gown (instead of a mannequin/dummy)

Videos should have at least 5 people in the frame for long intervals for sufficient subset of frames that we can sample from surgeons should be wearing the gowns that they normally would If surgeons are wearing COVID headgear during surgery, they should wear it here too Lighting in these videos should replicate what is to be expected in a real-life setting.

Bounding box annotation can be conducted, for example, using tools such as Scaleabel, and remote access to various AI servers on-site can be used for annotation and training, using tools such as SSH and VNC to obtain access.

For model fine-tuning, the head detection model can be trained and validated by Detectron2 (e.g., from https://github.com/facebookresearch/detectron2), and the backbone model can be ResNet 101 with FPN pre-trained on head detection dataset from existing sites.

In some embodiments, as data should not be leaving the site, the site can have a site-specific data policy, and information gained from a particular site could be configured to avoid integration into a general model. Rather, in some embodiments, a site-specific model can be trained and validated by the data requested above.

In terms of testing, the fine-tuned model can be tested by split tests, among other approaches. Ideally, data in test set should come from different case other than the training/validation set.

Quality Assurance Approach

As described above, the output data set (e.g., video) after pre-processing may not yield a fully de-identified video. To minimize the cost of analyst work, quality assurance analysts can utilize tools such as video editors, for example, iMovie, After Effects or Final Cut Pro that can be utilized to post-process the videos, noting down in the images, where and how the model fails, which can then be used as feedback for improving the model.

For example, when using After Effects, the video can be dragged into a timeline area to begin the quality assurance process, and different layers and fill shapes can then be established for a period of time to block still objects.

In respect of moving heads/body segmentation, roto brush tools can be used such that on a first frame, an anchor is established, with a fine segmentation, and a propagated mask can be used to track an object through multiple frames for a duration of time. For example, an "effect opacity" characteristic can be selected (e.g., 75%), and the layers can be composited together.

Similarly, "light camera" techniques can be used in regions where operations are occurring, such that other areas are blocked. In the tool, ellipses can be drawn in regions where aspects need to be revealed, and then Alpha Matte attributes and/or other aspects can be establish shapes for being revealed. If an identifiable feature or shape is shown in the revealed region, another shape layer can be used be placed over the other shape to cover the shape.

In areas requiring retouching by a quality assurance person, a data set for collecting failure cases of the model can be tracked to help understand when the model is not performing well to corner cases various. Adding these frame samples to the training data can help improve the model.

A feedback data set can include spreadsheets or other types of data structures or data objects, tracking, for example, the following fields for head and body de-identification issues:

video name: file name of the video timestamp: the second where the model fails class label: the class (surgical team, patient, others) which the model fails decryption: detailed information about the failure, indicating which person was shown, possible reason, etc.

3D Camera Examples

In a further variant embodiment, an approach to de-identification is provided using three-dimensional cameras (that include a fourth dimension representing depth to the typical RGB [red, green, blue] video recordings). The use of 3D cameras in de-identification can be helpful in respect of human detection. In another variation, camera information can be appended with additional depth camera to simulate a 3D camera input in respect of the de-identification system.

Figure 17:
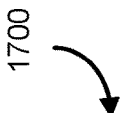
FIG. 17 shows an example output frame of the system, according to an experiment.

FIG. 17 shows an example output frame of the system, according to an experiment. In FIG. 17, it can be observed from the output 1700 that the bodies of a number of practitioners have been partially cartoonified, and the detected head regions have been replaced with rectilinear mask shapes that have completely replaced the pixels.

Figure 18:
FIG. 18 shows another example output frame of the system, according to an experiment where a practitioner is moving.

FIG. 18 shows another example output frame of the system, according to an experiment where a practitioner is moving. In FIG. 18, it can be observed from the output 1800 that the bodies of a number of practitioners have also been partially cartoonified, and the detected head regions have been replaced with rectilinear mask shapes that have completely replaced the pixels.

In FIG. 18, as the practitioner on the left is moving, momentum extrapolation has been utilized to create an additional region of uncertainty around the body contour and the head bounding box such that both of the head bounding box and the body contour sizes have been increased. In FIG. 18, the increased regions of the body contour can, for example, be applied a different threshold contribution score during the model output weighting process to indicate that these are merely areas of uncertainty.

Figure 19:
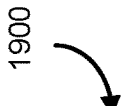
FIG. 19 is an example mask array generated through de-identification, according to some embodiments.

FIG. 19 is an example mask array generated through de-identification, according to some embodiments. In FIG. 19, a number of contribution scores are shown in the array 1900 for the encoding, and the encoding can be different as described earlier in respect of different thresholds. In FIG. 19, for example the middle region of 1s correspond to a head bounding box, which has a value of 1 and the pixels will have a maximum level of obfuscation. The other regions having values between 0.5 and 0.8 for example, can be cartoonized as they may correspond to body parts, and between 0.0 and 0.5 could be blurred as they are potentially identify-able but may be of lower importance (e.g., clock face types). Similarly, for genital regions or other sensitive regions, they may also be applied a score of 1 for full obfuscation.

REFERENCES

[1] Alp Güler, Riza and Neverova, Natalia and Kokkinos, Iasonas. Densepose: Dense human pose estimation in the wild. *Proceedings of the IEEE Conference on Computer Vision and Pattern Recognition*, pages 7297-7306, 2018.

[2] Biadsy, Fadi and Weiss, Ron J and Moreno, Pedro J and Kanvesky, Dimitri and Jia, Ye. Parrotron: An end-to-end speech-to-speech conversion model and its applications to hearing-impaired speech and speech separation. *arXiv preprint arXiv:* 1904.04169, 2019.

[3] Bochinski, Erik and Eiselein, Volker and Sikora, Thomas. High-speed tracking-by-detection without using image information. 2017 14*th IEEE International Conference on Advanced Video and Signal Based Surveillance (AVSS)*, pages 1-6, 2017. IEEE.

[4] Feichtenhofer, Christoph and Pinz, Axel and Zisserman, Andrew. Detect to track and track to detect. *Proceedings of the IEEE International Conference on Computer Vision*, pages 3038-3046, 2017.

[5] Evangello Flouty and Odysseas Zisimopoulos and Danail Stoyanov. FaceOff: Anonymizing Videos in the Operating Rooms. 2018.

[6] He, Kaiming and Gkioxari, Georgia and Dollar, Piotr and Girshick, Ross. Mask r-cnn. *Proceedings of the IEEE international conference on computer vision*, pages 2961-2969, 2017.

[7] He, Kaiming and Zhang, Xiangyu and Ren, Shaoqing and Sun, Jian. Deep residual learning for image recognition. *Proceedings of the IEEE conference on computer vision and pattern recognition*, pages 770-778, 2016.

[8] Jia, Ye and Zhang, Yu and Weiss, Ron and Wang, Quan and Shen, Jonathan and Ren, Fei and Nguyen, Patrick and Pang, Ruoming and Moreno, Ignacio Lopez and Wu, Yonghui and others. Transfer learning from speaker verification to multispeaker text-to-speech synthesis. *Advances in neural information processing systems*, pages 4480-4490, 2018.

[9] Lin, Tsung-Yi and Dollar, Piotr and Girshick, Ross and He, Kaiming and Hariharan, Bharath and Belongie, Serge. Feature pyramid networks for object detection. *Proceedings of the IEEE conference on computer vision and pattern recognition*, pages 2117-2125, 2017.

[10] Lin, Tsung-Yi and Maire, Michael and Belongie, Serge and Hays, James and Perona, Pietro and Ramanan, Deva and Dollar, Piotr and Zitnick, C Lawrence. Microsoft coco: Common objects in context. *European conference on computer vision*, pages 740-755, 2014. Springer.

[11] Loper, Matthew and Mahmood, Naureen and Romero, Javier and Pons-Moll, Gerard and Black, Michael J. SMPL: A skinned multi-person linear model. *ACM transactions on graphics (TOG)*, 34(6): 1-16, 2015.

[12] Menon, Raghav and Kamper, Herman and Quinn, John and Niesler, Thomas. Fast ASR-free and almost zero-resource keyword spotting using DTW and CNNs for humanitarian monitoring. *arXiv preprint arXiv: 1806.09374*, 2018.

[13] Prenger, Ryan and Valle, Rafael and Catanzaro, Bryan. Waveglow: A flow-based generative network for speech synthesis. *ICASSP 2019-2019 IEEE International Conference on Acoustics, Speech and Signal Processing (ICASSP)*, pages 3617-3621, 2019. IEEE.

[14] Ravanelli, Mirco and Parcollet, Titouan and Bengio, Yoshua. The pytorch-kaldi speech recognition toolkit. *ICASSP 2019-2019 IEEE International Conference on Acoustics, Speech and Signal Processing (ICASSP)*, pages 6465-6469, 2019. IEEE.

[15] Ren, Shaoqing and He, Kaiming and Girshick, Ross and Sun, Jian. Faster r-cnn: Towards real-time object detection with region proposal networks. *Advances in neural information processing systems*, pages 91-99, 2015.

[16] Shen, Jonathan and Pang, Ruoming and Weiss, Ron J and Schuster, Mike and Jaitly, Navdeep and Yang, Zongheng and Chen, Zhifeng and Zhang, Yu and Wang, Yuxuan and Skerrv-Ryan, Rj and others. Natural tts synthesis by conditioning wavenet on mel spectrogram predictions. 2018 *IEEE International Conference on Acoustics, Speech and Signal Processing (ICASSP)*, pages 4779-4783, 2018. IEEE.

[17] Silas, Megan R and Grassia, Philippe and Langerman, Alexander. Video recording of the operating room; is anonymity possible? *Journal of Surgical Research*, 197(2):272-276, 2015.

[18] Thies, Justus and Elgharib, Mohamed and Tewari, Ayush and Theobalt, Christian and Nießner, Matthias. Neural voice puppetry: Audio-driven facial re-enactment. *arXiv preprint arXiv:1912.05566*, 2019.

The term "connected" or "coupled to" may include both direct coupling (in which two elements that are coupled to each other contact each other) and indirect coupling (in which at least one additional element is located between the two elements).

Although the embodiments have been described in detail, it should be understood that various changes, substitutions and alterations can be made herein without departing from the scope. Moreover, the scope of the present application is not intended to be limited to the particular embodiments of the process, machine, manufacture, composition of matter, means, methods and steps described in the specification.

As one will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the embodiments described herein are intended to include within their scope such processes, machines, manufacture, compositions of matter, means, methods, or steps.

As can be understood, the examples described above and illustrated are intended to be exemplary only.

What is claimed is:

1. A system for de-identifying raw data including audio or video from one or more input video streams having one or more visual or audible identifiable artifacts, the system comprising:

a computer processor coupled to a computer memory and one or more non-transitory computer readable media, the computer processor configured to:

maintain a machine learning model architecture configured to track one or more audio or visual artifacts present in the one or more input video streams and to identify the one or more audio or visual identifiable artifacts as objects for de-identification;

transform portions of frames of the one or more input video streams to replace the one or more audio or visual identifiable artifacts with corresponding obfuscated replacement audio or visual artifacts; and generate one or more output video streams including the transformed portions of the frames of the one or more input video streams having the obfuscated replacement audio or visual artifacts;

wherein momentum-based interpolation is utilized to establish one or more boundaries providing a temporal, visual, or frequency-based margin around the one or more audio or visual identifiable artifacts for generating the corresponding obfuscated replacement audio or visual artifacts; and wherein the temporal, visual, or frequency-based margin is utilized to include an additional region for expanding the corresponding obfuscated replacement audio or visual artifacts;

wherein the momentum-based interpolation includes using head tracking based on an average displacement of a bounding box between the frames of the one or more input video streams, extending a blurred field around an individual as the individual moves with a degree of extension positively correlated with a speed of the individual.

2. The system of claim 1, wherein the computer processor is configured to transform portions of the frames of the one or more input video streams by replacing detected visual objects corresponding to bodies of practitioners with contour maps established around a pixel boundary corresponding to the bodies of the practitioners.

3. The system of claim 1, wherein the computer processor is configured to transform portions of the frames of the one or more input video streams by replacing detected visual objects corresponding to heads of practitioners with blurred visual blocks established around a pixel boundary corresponding to the heads of the practitioners.

4. The system of claim 1, wherein an inference subnet is configured to use the momentum-based interpolation during head detection, and the head detection is only run on sampled frames and intervening frames which are required to be smoothed or interpolated.

5. The system of claim 1, wherein a size of the bounding box is dynamically modified responsive to a detected inconsistency between the frames.

6. The system of claim 1, wherein the machine learning model architecture is tunable through modification of one or more hyperparameters to modify a balance between false positives and false negatives.

7. The system of claim 1, wherein the one or more output video streams are transmitted to a downstream analytic computing system configured for replay of the one or more output video streams having one or more automatically appended predictive annotations indicative of one or more key sections of the one or more output video streams for analysis.

8. The system of claim 7, wherein for the one or more key sections, a different balance between false positives and false negatives is applied relative to one or more non-key sections of the one or more output video streams.

9. The system of claim 1, wherein the one or more output video streams are generated for real or near-real time analysis, and one or more refined output video streams are generated with different parameters for batch analysis.

10. The system of claim 9, wherein the one or more refined output video streams include less obfuscated audio or video features relative to the one or more output video streams generated for the real or near-real time analysis.

11. A method for de-identifying raw data including audio or video from one or more input video streams having one or more visual or audible identifiable artifacts, the method comprising:

maintaining a machine learning model architecture configured to track one or more audio or visual artifacts present in the one or more input video streams and to identify the one or more audio or visual identifiable artifacts as objects for de-identification;

transforming portions of frames of the one or more input video streams to replace the one or more audio or visual identifiable artifacts with corresponding obfuscated replacement audio or visual artifacts; and generating one or more output video streams including the transformed portions of the frames of the one or more input video streams having the obfuscated replacement audio or visual artifacts;

wherein momentum-based interpolation is utilized to establish one or more boundaries providing a temporal, visual, or frequency-based margin around the one or more audio or visual identifiable artifacts for generating the corresponding obfuscated replacement audio or visual artifacts; and wherein the temporal, visual, or frequency-based margin is utilized to include an additional region for expanding the corresponding obfuscated replacement audio or visual artifacts;

wherein the momentum-based interpolation includes using head tracking based on an average displacement of a bounding box between the frames of the one or more input video streams, extending a blurred field around an individual as the individual moves with a degree of extension positively correlated with a speed of the individual.

12. The method of claim 11, wherein the computer processor is configured to transform portions of the frames of the one or more input video streams by replacing detected visual objects corresponding to bodies of practitioners with contour maps established around a pixel boundary corresponding to the bodies of the practitioners.

13. The method of claim 11, wherein the computer processor is configured to transform portions of the frames of the one or more input video streams by replacing detected visual objects corresponding to heads of practitioners with blurred visual blocks established around a pixel boundary corresponding to the heads of the practitioners.

14. The method of claim 11, wherein an inference subnet is configured to use the momentum-based interpolation during head detection, and the head detection is only run on sampled frames and intervening frames which are required to be smoothed or interpolated.

15. The method of claim 11, wherein a size of the bounding box is dynamically modified responsive to a detected inconsistency between the frames.

16. The method of claim 11, wherein the machine learning model architecture is tunable through modification of one or more hyperparameters to modify a balance between false positives and false negatives.

17. The method of claim 11, wherein the one or more output video streams are transmitted to a downstream analytic computing system configured for replay of the one or more output video streams having one or more automatically appended predictive annotations indicative of one or more key sections of the one or more output video streams for analysis.

18. The method of claim 17, wherein for the one or more key sections, a different balance between false positives and false negatives is applied relative to one or more non-key sections of the one or more output video streams.

19. The method of claim 11, wherein the one or more output video streams are generated for real or near-real time analysis, and one or more refined output video streams are generated with different parameters for batch analysis.

20. A non-transitory computer readable medium storing machine interpretable instructions, which when executed by a processor, cause the processor to perform a method for de-identifying raw data including audio or video from one or more input video streams having one or more visual or audible identifiable artifacts, the method comprising:

maintaining a machine learning model architecture configured to track one or more audio or visual artifacts present in the one or more input video streams and to identify the one or more audio or visual identifiable artifacts as objects for de-identification;

transforming portions of frames of the one or more input video streams to replace the one or more audio or visual identifiable artifacts with corresponding obfuscated replacement audio or visual artifacts; and generating one or more output video streams including the transformed portions of the frames of the one or more input video streams having the obfuscated replacement audio or visual artifacts;

wherein momentum-based interpolation is utilized to establish one or more boundaries providing a temporal, visual, or frequency-based margin around the one or more audio or visual identifiable artifacts for generating the corresponding obfuscated replacement audio or visual artifacts; and wherein the temporal, visual, or frequency-based margin is utilized to include an additional region for expanding the corresponding obfuscated replacement audio or visual artifacts;

wherein the momentum-based interpolation includes using head tracking based on an average displacement of a bounding box between the frames of the one or more input video streams, extending a blurred field around an individual as the individual moves with a degree of extension positively correlated with a speed of the individual.

* * * * *